(12) United States Patent
Lowry et al.

(10) Patent No.: US 8,163,021 B2
(45) Date of Patent: Apr. 24, 2012

(54) METHODS AND SYSTEMS FOR REPAIRING AN INTERVERTEBRAL DISC USING A TRANSCORPORAL APPROACH

(75) Inventors: David Lowry, Holland, MI (US); Desmond O'Farrell, Grand Rapids, MI (US); Scott Tuinstra, Holland, MI (US); Roger Veldman, Hudsonville, MI (US)

(73) Assignee: Transcorp, Inc., Ada, MI (US)

( * ) Notice: Subject to any disclaimer, the term of this patent is extended or adjusted under 35 U.S.C. 154(b) by 548 days.

(21) Appl. No.: 12/323,361

(22) Filed: Nov. 25, 2008

(65) Prior Publication Data

US 2009/0143716 A1 Jun. 4, 2009

Related U.S. Application Data

(60) Provisional application No. 60/990,587, filed on Nov. 27, 2007.

(51) Int. Cl.
*A61F 2/44* (2006.01)
(52) U.S. Cl. ..................................... 623/17.11
(58) Field of Classification Search ..... 623/17.11–17.16
See application file for complete search history.

(56) References Cited

U.S. PATENT DOCUMENTS

| | | |
|---|---|---|
| 3,741,205 A | 6/1973 | Markolf et al. |
| 5,059,194 A | 10/1991 | Michelson |
| 5,246,458 A | 9/1993 | Graham |
| 5,306,275 A | 4/1994 | Bryan |
| 5,423,826 A | 6/1995 | Coates et al. |
| 5,486,180 A | 1/1996 | Dietz et al. |
| 5,489,307 A | 2/1996 | Kuslich et al. |
| 5,505,732 A | 4/1996 | Michelson |
| 5,645,599 A | 7/1997 | Samani |
| 5,722,977 A | 3/1998 | Wilhelmy |
| 5,741,253 A | 4/1998 | Michelson |
| 5,772,661 A | 6/1998 | Michelson |
| 5,795,291 A | 8/1998 | Koros |
| 5,797,909 A | 8/1998 | Michelson |

(Continued)

FOREIGN PATENT DOCUMENTS

DE 4434384 A1 3/1996

(Continued)

OTHER PUBLICATIONS

O'Farrell et al.; U.S. Appl No. 12/783,499 entitled "Implantable vertebral frame systems and related methods for spinal repair," filed May 19, 2010.

(Continued)

*Primary Examiner* — Eduardo C Robert
*Assistant Examiner* — Summer Kostelnik
(74) *Attorney, Agent, or Firm* — Shay Glenn LLP

(57) ABSTRACT

The invention includes a system and methods for performing surgery on a spinal disc. The system includes an implantable bone plate with an access port to accommodate a bone cutting device, a spinal repair device insertable through the access port of the bone plate configured to occupy a surgically-formed vertebral channel from an anterior surface of the host vertebral body to a site central to an end plate of the host vertebral body, a trajectory control sleeve engageable to the bone plate to direct the trajectory of a cutting device, and a cutting device engageable within the trajectory control sleeve. Methods are directed to forming a vertebral channel and restoring the vertebral body and disc with devices that both repair the bone and the disc.

21 Claims, 19 Drawing Sheets

U.S. PATENT DOCUMENTS

| | | | |
|---|---|---|---|
| 5,800,433 A | 9/1998 | Benzel et al. | |
| 5,851,207 A | 12/1998 | Cesarone | |
| 5,893,890 A | 4/1999 | Pisharodi | |
| 5,984,922 A | 11/1999 | McKay | |
| 6,056,749 A | 5/2000 | Kuslich | |
| 6,066,142 A | 5/2000 | Serbousek | |
| 6,080,155 A | 6/2000 | Michelson | |
| 6,096,038 A | 8/2000 | Michelson | |
| 6,102,950 A | 8/2000 | Vaccaro | |
| 6,193,721 B1 | 2/2001 | Michelson | |
| 6,207,498 B1 | 3/2001 | Chen et al. | |
| 6,224,599 B1 | 5/2001 | Baynham et al. | |
| 6,224,607 B1 | 5/2001 | Michelson | |
| 6,231,610 B1 | 5/2001 | Geisler | |
| 6,241,733 B1 | 6/2001 | Nicholson et al. | |
| 6,258,094 B1 | 7/2001 | Nicholson et al. | |
| 6,261,293 B1 | 7/2001 | Nicholson et al. | |
| 6,287,313 B1 | 9/2001 | Sasso | |
| 6,315,795 B1 | 11/2001 | Scarborough et al. | |
| 6,332,887 B1 | 12/2001 | Knox et al. | |
| 6,342,056 B1 | 1/2002 | Mac-Thiong et al. | |
| 6,348,058 B1 | 2/2002 | Melkent et al. | |
| 6,371,986 B1 | 4/2002 | Bagby | |
| 6,383,186 B1 | 5/2002 | Michelson | |
| 6,385,475 B1 | 5/2002 | Cinquin et al. | |
| 6,440,139 B2 | 8/2002 | Michelson | |
| 6,447,544 B1 | 9/2002 | Michelson | |
| 6,461,359 B1 | 10/2002 | Tribus et al. | |
| 6,517,544 B1 | 2/2003 | Michelson | |
| 6,558,390 B2 | 5/2003 | Cragg | |
| 6,562,046 B2 | 5/2003 | Sasso | |
| 6,562,074 B2 | 5/2003 | Gerbec et al. | |
| 6,579,290 B1 | 6/2003 | Hardcastle et al. | |
| 6,599,292 B1 | 7/2003 | Ray | |
| 6,607,530 B1 | 8/2003 | Carl et al. | |
| 6,648,917 B2 | 11/2003 | Gerbec et al. | |
| 6,663,637 B2 | 12/2003 | Dixon et al. | |
| 6,709,438 B2 | 3/2004 | Dixon et al. | |
| 6,740,087 B2 | 5/2004 | Knox | |
| 6,770,074 B2 | 8/2004 | Michelson | |
| 6,837,905 B1 | 1/2005 | Lieberman | |
| 6,859,661 B2 | 2/2005 | Tuke | |
| 6,923,811 B1 | 8/2005 | Carl et al. | |
| 7,014,633 B2 | 3/2006 | Cragg | |
| 7,033,362 B2 | 4/2006 | McGahan et al. | |
| 7,081,119 B2 | 7/2006 | Stihl | |
| 7,083,623 B2 | 8/2006 | Michelson | |
| 7,153,304 B2 | 12/2006 | Robie et al. | |
| 7,163,542 B2 | 1/2007 | Ryan | |
| 7,179,225 B2 | 2/2007 | Shluzas et al. | |
| 7,207,991 B2 | 4/2007 | Michelson | |
| 7,303,565 B2 | 12/2007 | Buttermann et al. | |
| 2001/0047172 A1 | 11/2001 | Foley et al. | |
| 2003/0055427 A1 | 3/2003 | Graf | |
| 2003/0060825 A1 | 3/2003 | Alfaro et al. | |
| 2003/0060828 A1 | 3/2003 | Michelson | |
| 2003/0149341 A1 | 8/2003 | Clifton | |
| 2003/0187441 A1 | 10/2003 | Bolger et al. | |
| 2003/0236526 A1 | 12/2003 | Van Hoeck et al. | |
| 2004/0006343 A1 | 1/2004 | Sevrain | |
| 2004/0097925 A1 | 5/2004 | Boehm et al. | |
| 2004/0106924 A1 | 6/2004 | Ralph et al. | |
| 2004/0106927 A1 | 6/2004 | Ruffner et al. | |
| 2004/0106997 A1 | 6/2004 | Lieberson | |
| 2004/0153089 A1 | 8/2004 | Zdeblick et al. | |
| 2004/0204717 A1 | 10/2004 | Fanger et al. | |
| 2004/0215203 A1 | 10/2004 | Michelson | |
| 2004/0267274 A1 | 12/2004 | Patel et al. | |
| 2005/0043738 A1 | 2/2005 | Ryan | |
| 2005/0043740 A1 | 2/2005 | Haid et al. | |
| 2005/0149026 A1 | 7/2005 | Butler et al. | |
| 2005/0149046 A1 | 7/2005 | Friedman et al. | |
| 2005/0267481 A1 | 12/2005 | Carl et al. | |
| 2005/0277921 A1 | 12/2005 | Eisermann et al. | |
| 2006/0030858 A1 | 2/2006 | Simonson et al. | |
| 2006/0036247 A1 | 2/2006 | Michelson | |
| 2006/0074424 A1 | 4/2006 | Alleyne et al. | |
| 2006/0084844 A1 | 4/2006 | Nehls | |
| 2006/0094951 A1 | 5/2006 | Dean et al. | |
| 2006/0122701 A1 | 6/2006 | Kiester | |
| 2006/0122704 A1* | 6/2006 | Vresilovic et al. | 623/17.16 |
| 2006/0136058 A1 | 6/2006 | Pietrzak | |
| 2006/0149251 A1 | 7/2006 | Ziolo et al. | |
| 2006/0167457 A1 | 7/2006 | Suddaby | |
| 2006/0235398 A1 | 10/2006 | Farris et al. | |
| 2006/0241646 A1 | 10/2006 | Stihl | |
| 2006/0247630 A1 | 11/2006 | Iott et al. | |
| 2006/0247654 A1 | 11/2006 | Berry | |
| 2006/0271198 A1 | 11/2006 | McAfee | |
| 2006/0276794 A1 | 12/2006 | Stern | |
| 2007/0118219 A1 | 5/2007 | Hyde, Jr. | |
| 2007/0173842 A1 | 7/2007 | Abdou | |
| 2007/0233107 A1 | 10/2007 | Zielinski | |
| 2007/0233260 A1* | 10/2007 | Cragg | 623/17.12 |
| 2007/0270851 A1 | 11/2007 | Erickson et al. | |
| 2008/0039847 A1 | 2/2008 | Piper et al. | |
| 2008/0045966 A1 | 2/2008 | Buttermann et al. | |
| 2008/0269806 A1 | 10/2008 | Zhang et al. | |
| 2008/0312744 A1* | 12/2008 | Vresilovic et al. | 623/17.16 |
| 2009/0171396 A1 | 7/2009 | Baynham et al. | |
| 2009/0187191 A1* | 7/2009 | Carl et al. | 606/80 |
| 2010/0057134 A1 | 3/2010 | Lowry et al. | |
| 2010/0152784 A1 | 6/2010 | Lowry et al. | |
| 2010/0152793 A1 | 6/2010 | Lowry et al. | |

FOREIGN PATENT DOCUMENTS

| | | |
|---|---|---|
| DE | 10307758 A1 | 9/2004 |
| EP | 0890341 A1 | 1/1999 |
| FR | 2727005 A1 | 5/1996 |
| SU | 1424826 A1 | 9/1988 |
| WO | WO97/06753 A2 | 2/1997 |
| WO | WO98/14142 A1 | 4/1998 |
| WO | WO02/09626 A1 | 2/2002 |
| WO | WO02/069811 | 9/2002 |
| WO | WO 02/080789 A1 | 10/2002 |
| WO | WO03/075774 A1 | 9/2003 |
| WO | WO2006/020531 A2 | 2/2006 |
| WO | WO2006/058079 A2 | 6/2006 |
| WO | WO2007/002251 | 1/2007 |
| WO | WO2007/018458 A1 | 2/2007 |
| WO | WO2007/019631 A1 | 2/2007 |
| WO | WO2007/079242 A2 | 7/2007 |
| WO | WO2007/084427 A2 | 7/2007 |
| WO | WO2007/089858 A2 | 8/2007 |

OTHER PUBLICATIONS

Lowry et al.; U.S. Appl. No. 11/855,124 entitled "Implantable bone plate system and related method for spinal repair," filed Sep. 13, 2007.

Lowry et al.; U.S. Appl. No. 12/188,131 entitled "Device and method for variably adjusting intervertebral distraction and lordosis," filed Aug. 7, 2008.

Lowry et al.; U.S. Appl. No. 12/210,109 entitled "Device and method for tissue retraction in spinal surgery," filed Sep. 12, 2008.

Lowry et al.; U.S. Appl. No. 12/210,089 entitled "Transcorporeal spinal decompression and repair system and related method," filed Sep. 12, 2008.

Lowry et al.; U.S. Appl. No. 12/239,431 entitled "Vertebrally-mounted tissue retractor and method for use in spinal surgery," filed Sep. 26, 2008.

Choi et al.; Modified transcorporeal anterior cervical microforaminotomy for cervical radiculopathy: a technical note and early results; Eur. Spine. J.; vol. 16; pp. 1387-1393; 2007.

George et al.; Oblique transcorporeal approach to anteriorly located lesions in the cervical spinal canal; Acta. Neurochir. (Wien); vol. 121; pp. 187-190; 1993.

George et al.; Oblique transcorporeal drilling to treat anterior compression of the spinal cord at the cervical level; Minim. Invas. Neurosurg.; vol. 37; pp. 48-52; 1994.

Hong et al.; Comparison between transuncal approach and upper vertebral transcorporeal approach for unilateral cervical radiculopathy—a preliminary report; Minim. Invas. Neurosurg.; vol. 49; pp. 296-301; 2006.

Jho et al.; Ventral uncoforaminotomy; J. Neurosurg. Spine; vol. 7; pp. 533-536; 2007.

Jho et al.; Anterior microforaminotomy for treatment of cervical radiculopathy: part 1—disc-preserving functional cervical disc surgery; Neurosurgery; vol. 51; supp. 2; pp. S-46-53; Nov. 2002.

Kim et al.; Anterior decompression via a wide transvertebral approach and a ceramic insert in a patient with cervical degenerative disease; Surgical neurology; vol. 67; pp. 127-134; 2007.

Wolf et al.; MBARS: mini bone-attached robotic system for joint arthroplasty; Int. J. Medical Robotics and Computer Assisted Surgery; vol. 1; No. 2; pp. 101-121; 2005.

* cited by examiner

METHODS AND SYSTEMS FOR REPAIRING AN INTERVERTEBRAL DISC USING A TRANSCORPORAL APPROACH

CROSS REFERENCE TO RELATED APPLICATIONS

This application claims priority to U.S. Provisional Patent Application No. 60/990,587 of Lowry et al., entitled "Methods and Systems for Repairing an Intervertebral Disc Using a Transcorporal Approach", as filed on Nov. 27, 2007.

FIELD OF INVENTION

The invention relates to a system and methods of spinal surgery. More particularly, the invention provides a system, devices, and methods to create a surgical access channel between a surgically-exposed surface of a vertebra and the end plate bone tissue of the vertebra adjacent the degenerated disc.

INCORPORATION BY REFERENCE

All publications, patents and patent applications mentioned in this specification, either by inventors common to this application or other inventors, are herein incorporated by reference to the same extent as if each individual publication, patent or patent application was specifically and individually indicated to be incorporated by reference.

In particular, the following U.S. Patent Applications include related subject matter, and are incorporated in their entirety by this reference: U.S. patent application Ser. No. 11/855,124 of Lowry et al. (filed on Sep. 13, 2007, and entitled "Implantable bone plate system and related method for spinal repair"), U.S. patent application Ser. No. 12/210,109 of Lowry et al. (filed on Sep. 12, 2008, entitled "Device and method for tissue retraction in spinal surgery"), U.S. patent application Ser. No. 12/210,089 of Lowry et al. (filed on Sep. 12, 2008, entitled "Transcorporeal spinal decompression and repair system and related method"), and U.S. patent application Ser. No. 12/239,431 of Lowry et al. (filed on Sep. 26, 2008, entitled "Vertebrally mounted tissue retractor and method for use in spinal surgery").

BACKGROUND OF THE INVENTION

Intervertebral discs provide articulating means and mechanical stress absorption in the spine and further serve to permit controlled motion across vertebral segments. Vertebral discs degenerate progressively as a result of the natural aging process, and injury or disease, and with physical degeneration comes a loss in thickness or height of the disc, and a loss in their capacity to support a load and to absorb shock. Physically, disc degeneration can present in the form of the disc bulging material beyond its normal anatomical space or with collapse of the disc, both conditions being associated with spinal stenosis. Degenerative disc disease is variously associated with axial neck or back pain, a loss of normal spinal motion or increased abnormal motion, back pain, numbness, tingling, or weakness in one or more limbs.

In other instances a sudden physical stress on the spine can cause a defect to occur on the fibrous outer ring of the disc, the annulus fibrosis. In these cases the inner disc material, the nucleus pulposus, can rupture or protrude beyond the outer surface of the annulus, or shift outward a portion of the ring of the annulus fibrosis, resulting in an impingement on an adjacent neural structure. This is commonly referred to as a disc herniation, protrusion, or rupture, and typically causes symptoms similar to those of degenerative disc disease.

Nerve root impingements related to disc degeneration can occur throughout the spine but are most common in the lumbar and cervical regions. Most symptomatic disc degenerations occur posteriorly, and are thus particularly problematic as they are immediately adjacent to the spinal cord and nerve roots, and thereby prone to inducing neural impingement.

There are various treatment options for degenerative disc disease and disc herniations. Mild degenerative disc disease is often treated non-surgically, but more severe cases often require surgical treatment. These treatments may include the removal of the disc (discectomy), a reconditioning of the disc using a synthetic substance added to the nucleus (nucleoplasty), artificial total disc replacement (arthroplasty), or a spinal fusion procedure (arthrodesis). Recent trends in spine surgical development have focused on the replacement or repair of damaged discs with various biocompatible implants or repair devices. While a total disc arthroplasty in the cervical spine is presently done from an anterior surgical approach to the spine, a reconditioning of any disc may be achieved injecting an artificial nucleus pulposus material through a defect surgically created in the annulus fibrosis in the course of resecting compressing disc material.

Presently, current techniques for reconditioning the nucleus pulposus with a synthetic material or performing a total disc arthroplasty (disc replacement) require that a defect be made in the outer rim of the disc, the annulus fibrosis. The annulus defect may be several millimeters wide, as when injecting a nucleus reconditioning substance such as NuCore (Spine Wave, Inc., Shelton, Conn.), or it may be as large as several centimeters, as when doing a disc arthroplasty. Any defect in the annulus, however, can initiate a post-operative herniation or migration of the implanted reconditioning substance out of the normal interior space of the disc. This undesirable result can induce a compression of an adjacent neural structure and/or induce a collapse of the intervertebral disc.

Some improvements have been made in surgical approaches to disc damage or disease, as exemplified by U.S. Pat. App. No. 2006/0271198 of McAfee, U.S. Pat. App. No. 2005/0149046 of Friedman, and U.S. Pat. App. No. 2006/0074424 of Alleyne. There remains a need, however, specifically for approaches by which the inner portion, the nucleus pulposus, of the vertebral discs, particularly cervical discs, can be accessed and repaired, restored, or replaced without violating the annulus fibrosis of the disc.

SUMMARY OF THE INVENTION

The invention provides a system with devices and methods by which to utilize the system and devices to form and repair an intervertebral channel useful in surgical procedures involving repair or replacement of at least a portion of the intervertebral disc, such portion typically involving the central portion of the disc, the nucleus pulposus. The channel is transcorporal in nature, i.e., it traverses through a vertebral body and approaches the disc from a central aspect that preserves the integrity of the peripheral portion of the disc, the annulus fibrosis. Embodiments of the invention also include repair devices that fill the channel once the channel has fulfilled its function as well as substitute disc materials that functionally replace a damaged or excised portion of a disc. Embodiments of these bone repair devices include ones that have a lumen communicating between the proximal and distal ends of the device for the delivery of a flowable substitute disc material into the intervertebral space. Other bone repair device embodiments have a portion that occupies the transcorporal channel, but also another portion that extends into the intervertebral space to functionally replace a disc. Some of these latter embodiments may also include a lumen for the delivery of flowable substitute disc material that may augment support provided by the bone repair device itself, or help to support the integrity of the intervertebral space.

An embodiment of a spinal repair device, according to this invention, includes at least one lumen communicating between a proximal end of the device and a distal end of the device. The device embodiment is sized and configured to occupy at least a portion of a surgically-formed transcorporal channel in a vertebral body that extends on a trajectory from a non end-plate surface to an end plate where an opening of the channel communicates into an intervertebral space, the at least one lumen sized and configured to permit the flow therethrough of a disc replacement material. The trajectory of the channel, and by extension, the trajectory of a spinal repair device may be understood as a prescribed trajectory inasmuch as the optimal course of the channel and device are precisely planned by a surgeon prior to operating, such prescription based on the medical aspects and spinal dimensions of the patient.

With regard to the lumen or internal channel feature of the spinal repair device, in some embodiments, the at least one lumen provides a flow path for a liquid state disc repair material. In some embodiments, the lumen includes a flow prevention element that prevents egress of a liquid state disc repair material from the intervertebral space. And in some embodiments, the lumen includes two channels, a first channel configured for liquid flow into the intervertebral space, and a second channel configured to allow liquid or gas egress from the intervertebral space.

Some aspects and features of the implantable spinal repair device relate to the biocompatibility of the device and to its ability to integrate into the bone of the host vertebral body. Thus, in some embodiments, the device includes a surface portion that is sufficiently porous to allow in-growth of host bone. Some embodiments of the device include a biologically compatible material, which may include any of a polymer, a metal, a ceramic, or a combination thereof. In some embodiments, the device may include biologically absorbable material. Some embodiments of the device include an osteogenic agent incorporated into the device composition. In some embodiments, the device is formed in whole or in part from a porous cage, which permits passage of biological fluid and cells. In some of these embodiments, a bone cell preparation is included within the porous cage; these cells may be derived as an autograft preparation from the patient, from a compatible donor individual, and further, bone cells from any source may be cultured in an in vitro system prior to implantation.

With regard to the form and dimensions of the implantable bone repair device, some embodiments of the device are linear in form, such linear form configured to occupy a linear transcorporal channel. Other embodiments may be arcuate in form, such arcuate form configured to occupy an arcuate transcorporal channel. Embodiments of the device typically have a length that ranges from about 8 mm to about 20 mm and a diameter that ranges from about 3 mm and about 7 mm.

An embodiment of a system for spinal disc surgery, according to this invention, includes the above-summarized spinal repair device which includes the lumen, as well as a trajectory control apparatus adapted to attach to the non-end plate surface of the vertebral body and comprising a portion configured to hold at least a portion of a bone cutting tool such that when the apparatus is engaged to the vertebral body, the bone cutting tool is positioned to form the transcorporal channel. In these embodiments of a system, the trajectory control apparatus includes a cutting tool holder portion and an implantable bone plate portion; the cutting tool holding portion is detachably engageable to the implantable bone plate portion. Some embodiments of the cutting tool holder include a sleeve that receives at least a portion of a cutting tool. In some of these trajectory control apparatus embodiments, the cutting tool holder has a bone plate engagement feature and the bone plate has a cutting tool holder engagement feature; the respective engagement features are configured such that when the bone plate is attached to the vertebral body, and the cutting tool holder and the bone plate are mutually engaged, the cutting tool holder is oriented to direct a cutting tool on the trajectory. In some of these trajectory control apparatus embodiments, the bone plate portion includes an access port configured to accommodate a cutting portion of a bone cutting tool and to accommodate through passage of the spinal repair device.

Some embodiments of the system for spinal surgery include a bone cutting tool that is adapted to form the transcorporal channel; at least a portion of the bone cutting tool is configured to be movably held by the trajectory control apparatus. In some of these embodiments, the cutting tool includes a mechanical stop configured to limit the penetration of the cutting tool into the vertebral body.

Some embodiments of the system for spinal surgery include an injector that is configured to deliver a disc replacement material through the internal cannula of the spinal repair device and into an intradiscal void. These injector-including system embodiments may further include a valve device coupled with the injector, the valve device having at least two input ports and at least one output port (the output port being in fluid communication with the injector), a vacuum delivery device in fluid communication with one of the two input ports of the valve device, and a reservoir device containing the disc replacement material in communication with the second of the two input ports of the valve device. In some of these embodiments, the injector includes a channel that is configured to allow liquid or gas egress from the intervertebral space. In these injector-including embodiments, the disc replacement material is typically a flowable substance, which may include, for example, any of a liquid, a settable liquid, a liquid-to-solid phase changing material, a gel, a suspension, or a slurry.

An embodiment of a method for accessing and repairing an intervertebral disc in the spine, according to this invention, makes use of the above-summarized device which includes a lumen, and the summarized system that includes such a device. The method embodiment includes engaging a trajectory control apparatus to a non-endplate surface of a vertebral body; forming a transcorporal channel in a vertebral body with a trajectory that extends from a non end-plate surface to an end plate where a channel opening communicates into an intervertebral space; implanting into the transcorporal channel a spinal repair device sized and configured to occupy at least a portion of the channel; and injecting a disc replacement material through the spinal repair device and into a void within a space formerly occupied by at least a portion of the intervertebral disc. In some embodiments of this method, forming a transcorporal channel that extends from a non end-plate surface includes forming the channel from any of an anterior surface, a lateral surface, a posterior aspect of a pedicle, or a posterior, or posterolateral surface.

In some embodiments of the method, the engaging step includes implanting a bone plate portion of the trajectory control apparatus on the non-endplate surface of the vertebral body and then engaging a bone cutting tool holder portion of the trajectory control apparatus to the bone plate. In some of these embodiments, implanting a bone plate on the non-endplate surface of the vertebral body includes securing it to the surface with one or more fastening elements. And in some embodiments, the method may further include removing the bone plate after implanting it.

Some embodiments of method may also include removing at least a portion of the intervertebral disc through the transcorporal channel before injecting the disc replacement material, and in some of these particular embodiments, removing at least a portion of the intervertebral disc includes removing the nucleus pulposis and leaving the annulus fibrosis intact.

Some embodiments of the method may further include allowing gas from within the intervertebral space to escape through the spinal repair device during the injecting step. In some embodiments of the method, forming the transcorporal channel includes cutting bone with a bone-cutting tool. In some embodiments of the method, implanting the spinal repair device comprises compressively engaging an external surface of the spinal repair device with cancellous bone of the host vertebral body.

Another embodiment of a spinal repair device, according to this invention, includes a spinal repair device sized and configured to occupy at least a portion of a surgically-formed transcorporal channel in a host vertebral body and at least a portion of an intervertebral space adjacent the host vertebral body. This embodiment of the device has a proximal portion sized to occupy at least a portion of the transcorporal channel, the channel having a trajectory that extends from a non-end plate surface to an end plate where a channel opening communicates into the intervertebral space, and a distal portion sized to extend from the end plate of the host vertebral body into the intervertebral space. In some embodiments of this latter device, the distal portion extends to a point where it comes into intimate contact with an endplate of an adjacent vertebral body.

The proximal and distal portions various embodiments of the device may differ in composition, features, and function. For example, the proximal portion may be adapted to replace at least a portion of bone and the distal portion may be adapted to replace at least a portion of an intervertebral disc. In being adapted to generally replace bone or a portion of bone, at least the external surface of the proximal portion may be sufficiently porous to allow in-growth of bone. In some embodiments, the proximal portion of the device may include an osteogenic agent within its composition. Some embodiments of the proximal portion of the spinal repair device may include a porous cage, and some of these embodiments, a bone cell preparation may be included within that porous cage.

With regard to the distal portion of the spinal repair device, some embodiments may include a resilient composition that provides a shock-absorbing functionality similar to that of a healthy and intact disc. Some embodiments of the distal portion may include a distal surface adapted to articulatingly engage the end plate of the adjacent vertebral body, which can replicate the smooth low-friction slidable engagement that exists between a disc surface and vertebral end plates.

Some embodiments of the device are linear in form, such linear form configured to occupy a linear transcorporal channel. Other embodiments of the device are arcuate in form, such arcuate form configured to occupy an arcuate transcorporal channel. Some embodiments of this repair device, with distinct proximal and distal portions, may also include a lumen that communicates between an opening on the proximal end of the device and an opening distal end of the device, the channel comprising a flow path for a flowable disc replacement material.

With regard to the form and dimensions of the implantable bone repair device, some embodiments of the device are linear in form, such linear form configured to occupy a linear transcorporal channel. Other embodiments may be arcuate in form, such arcuate form configured to occupy an arcuate transcorporal channel. Embodiments of the device typically have a length that ranges from about 12 mm to about 25 mm and a diameter that ranges from about 3 mm to about 7 mm.

An embodiment of a system for spinal disc surgery, according to this invention, includes the above-summarized spinal repair device which includes a proximal portion within the transcorporal channel and a distal portion that extends into the intervertebral space, and further includes a trajectory control apparatus adapted to attach to the non-end plate surface of the vertebral body and comprising a portion configured to hold at least a portion of a bone cutting tool such that when the apparatus is engaged to the vertebral body, the bone cutting tool is positioned to form the transcorporal channel.

In some embodiments of this system, the trajectory control apparatus includes a cutting tool holder and an implantable bone plate portion, the cutting tool holding portion detachably engageable to the implantable bone plate portion. In various of these embodiments, the cutting tool holding portion includes a sleeve that receives at least a portion of a cutting tool. In some embodiments, the cutting tool holder has a bone plate engagement feature and the bone plate has a cutting tool holder engagement feature. These respective engagement features are configured such that when the bone plate is attached to the vertebral body, and the cutting tool holder and the bone plate are mutually engaged, the cutting tool holder is oriented to direct a cutting tool on the trajectory. In some embodiments of this system, the bone plate portion includes at least one access port configured to accommodate a cutting portion of a bone cutting tool and to accommodate through passage of the spinal repair device.

Some embodiments of the system of claim may include two spinal repair devices, the devices being configured to occupy dual surgically-formed transcorporal channels. These channels are typically parallel, and may be advantageous to the patient by providing bilateral support within a vertebral body.

Some embodiments of the system may further include a bone cutting tool that is adapted to form the transcorporal channel, and at least a portion of the bone cutting tool is configured to be accommodated by the trajectory control apparatus. In some embodiments, the cutting tool includes a mechanical stop configured to limit the penetration of the cutting tool into the host vertebral body.

Embodiments of the system may further include a disc replacement material which may be any of a liquid, a liquid that can solidify, a liquid-to-solid phase changing material, a fabric, or a solid, or any combination of these materials.

An embodiment of a method for accessing and repairing an intervertebral disc in the spine, according to this invention, makes use of the above-summarized spinal repair device which includes a proximal portion within the transcorporal channel and a distal portion that extends into the intervertebral space and the system that further includes the trajectory control apparatus that is adapted to attach to the non-end plate surface of a vertebral body and has a portion configured to hold at least a portion of a bone cutting tool. This method embodiment includes engaging a trajectory control apparatus to a surface of a host vertebral body; forming a transcorporal channel within a host vertebral body, the channel extending from a surface of the host vertebral body on a trajectory toward an intervertebral disc between the host vertebral body and an adjacent vertebral body, and extending at least as far as the end plate of the host vertebral body; replacing at least a portion of the disc; and implanting a spinal repair device configured to fit into the channel and extending into the intervertebral space.

In some embodiments of the method, forming a transcorporal channel that extends from a non end-plate surface includes forming the channel from any of an anterior surface, a lateral surface, a posterior aspect of a pedicle, or a posterior, or posterolateral surface. In some embodiments of the method, forming the transcorporal channel includes cutting bone with a bone-cutting tool.

In some embodiments of the method, implanting a spinal repair device includes placing a distal portion of the device in intimate contact with the end plate tissue of the vertebral body and a proximal portion in intimate contact with cancellous bone tissue within the transcorporal channel. In some embodiments of the method, implanting the spinal repair device comprises includes engaging an external surface of the spinal repair device with an internal surface of the transcorporal channel.

In some embodiments of the method, the engaging step may include implanting a bone plate portion of the trajectory control apparatus on the non-endplate surface of the vertebral body and then engaging a bone cutting tool holder portion of the trajectory control apparatus to the bone plate. In various of these embodiments, implanting a bone plate on the non-endplate surface of the vertebral body includes securing it to the surface with one or more fastening elements. And some embodiments of the method may further include removing the bone plate after implanting it. Such removal may occur at various points, such as after forming the transcorporal channel, after replacing a portion of the disc, or after implanting the spinal repair device.

Some embodiments of the method may further include removing at least a portion of the intervertebral disc through the transcorporal channel before implanting the spinal repair device. In particular embodiments of the method, removing a portion of a disc includes removing a nucleus pulposis and leaving an annulus fibrosis intact.

In some embodiments of the method, replacing at least a portion of the disc comprises replacing the portion of the disc with any of a any of a liquid, a liquid that can solidify, a liquid-to-solid phase changing material, a fabric, or a solid, or any combination of these materials. Some embodiments of the method may further include injecting a flowable disc material through a lumen in the spinal repair device into the intervertebral space.

Another embodiment of a system for spinal disc surgery includes a spinal repair device sized and configured to occupy at least a portion of a surgically-formed transcorporal channel in a vertebral body that extends on a trajectory from a non end-plate surface to an end plate where an opening communicates into an intervertebral space, a bone plate sized and configured to be implantable on a surface of the host vertebral body and configured to be engageable to a cutting tool holder, and a cutting tool holder configured to detachably engage the bone plate and configured to receive at least a portion of a bone cutting tool, the cutting tool holder, when engaged to the bone plate, positioned to guide the bone cutting tool to form the transcorporal channel with the trajectory. These system embodiments may further include a bone plate cover that is engageable to the bone plate and configured to cover an opening of the transcorporal channel on the non-endplate surface.

An embodiment of a method for accessing and repairing an intervertebral disc in the spine, according to this invention, makes use of the above-summarized system for spinal disc surgery which includes spinal repair device, a bone plate, and a cutting tool holder. This method embodiment includes engaging an implantable bone plate to a non-endplate surface of a vertebral body; detachably engaging a cutting tool holder to the implanted bone plate; forming a transcorporal channel in a vertebral body with a trajectory that extends from a non end-plate surface to an end plate where an opening communicates into an intervertebral space; implanting into the transcorporal channel a spinal repair device sized and configured to occupy at least a portion of the channel; and injecting a disc replacement material through the spinal repair device and into a void within a space formerly occupied by at least a portion of the intervertebral disc. Some of the embodiments of this method further include installing a bone plate cover on the bone plate and sealing an opening of the transcorporal channel on the non-endplate surface.

BRIEF DESCRIPTION OF THE DRAWINGS

FIG. 1B shows the transcorporal access channel expanded so as to include the central portion of an intervertebral disc.

FIG. 1C shows an injector penetrating the transcorporal access channel and delivering a disc repair material into the void within the disc, as in FIG. B.

FIG. 1D shows the injector (FIG. 1B) having been withdrawn, and the injected disc repair material having coalesced into a solid form.

FIG. 1E shows a bone repair implant being inserted into the transcorporal access channel.

FIG. 1F shows the bone repair implant completely in place, and its proximal end covered and secured by a bone plate that is attached to the vertebral body.

FIG. 24 shows the injection in progress, with a relatively small amount of disc material in the host site. FIG. 25 shows the host site nearly filled with substitute disc material.

DETAILED DESCRIPTION OF THE INVENTION

Figure 1A:
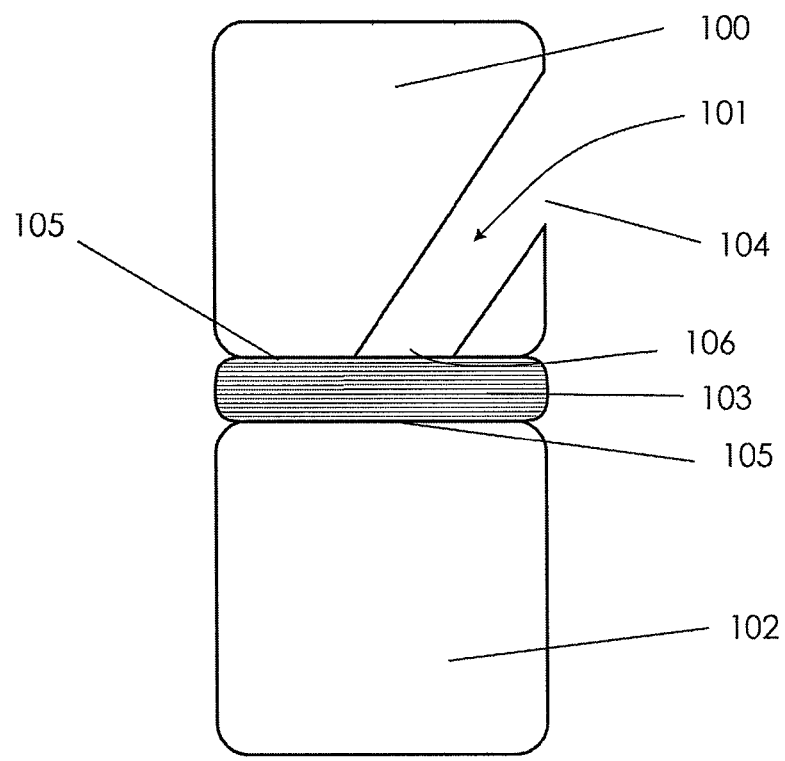
FIGS. 1A-1F are schematic cross-sectional views that storyboard a method for creating an transcorporal access channel within a vertebral body for accessing, repairing, replacing and/or restoring intervertebral disc tissue and thereafter repairing the intravertebral or transcorporal access channel with a bone repair material, and affixing an implantable bone plate to the surface of the vertebral bone tissue to prevent migration of the bone repair implant out of the intravertebral access channel.

The present invention provides a system, various devices, and methods to create and repair a transcorporal or intravertebral surgical access channel between a (1) surgically-exposed host vertebral body surface and (2) the end plate of the vertebral body that is adjacent to a disc in need of a surgical intervention, such as a degenerated disc. In some embodiments of the invention, the channel may be considered to extend beyond the vertebral body and into the intervertebral space, where a void has been created by removal or excision of at least a portion (the nucleus pulposus, for example) of the intervertebral disc. Accordingly, such a channel may be generally referred to as a vertebral repair channel, such channel also broadly including channels that are fully included within a single vertebral body, such as a transcorporal or intravertebral channel. These channels, formed by embodiments of devices and methods of the invention, may be used to provide surgical access to an intervertebral space, including access to a disc residing in the space, as well as to provide a host site for the implantation of a bone repair device, as per embodiments of devices provided by the invention.

An optimal surgical outcome, as provided by the invention, is one in which symptoms are relieved and the stability of the spine is improved. The physical bases of the functional or mechanical improvement provided by surgical procedures and devices provided herein includes the repairing, restoring, or replacing degenerated disc tissue, and restoring intervertebral height. In some embodiments, the procedure includes maintaining the integrity of annulus fibrosis of the disc, i.e., not disrupting the annulus fibrosis while replacing the nucleus pulposis within the annulus fibrosis with a substitute or replacement material or structure. In typical embodiments of the method, the repair of the transcorporal channel, used for surgical access to the intervertebral space or the disc therein, is filled in and restored to a state such that the former site of the channel poses no vulnerability. Devices included in a system that can implement the inventive method include various embodiments of an implantable bone repair device, an implantable bone plate, and a trajectory control sleeve, and a bone cutting tool, as described further below. In various embodiments of the invention, a trajectory control sleeve may also be referred to as a cutting tool holder; and in various embodiments of the invention, a cutting tool holder and a bone plate, particularly when joined together, may be understood to be portions of a single conjoined trajectory control apparatus. And these component portions, although identified separately, may also be referred to singularly in the conjoinable form as a trajectory control apparatus. Typical embodiments of a cutting tool holder do include a sleeve-like portion that holds at least a portion of a cutting tool during an aspect of the method when a transcorporal channel is being formed.

A transcorporal channel, as formed by method and device embodiments of the invention, allows direct access to the internal volume of the disc, more particularly to the nucleus pulposis of the disc, so that a disc repair, restoration or replacement procedure may be performed without penetrating or compromising the peripheral annulus fibrosis of the disc. Repair and restoration procedures may include the removal and replacement of nucleus pulposus tissue; the replacement materials may include solids, liquids, or phase-changing materials. The invention restores disc height, thus alleviating symptoms associated with degenerative disc disease. The method further and advantageously preserves a substantial amount of healthy disc tissue, more particularly, the method preserves the integrity of the annulus fibrosis and preserves healthy bone tissue, by virtue of the use of a transcorporal access pathway to the center of the disc, rather than a disruptive transdiscal approach. In terms of another benefit, the transcorporal approach contributes the net preservation or conservation of native bone and disc tissue compared to presently conventional surgical approaches.

In some embodiments, after completion of a disc repair procedure, a bone repair implant formed from natural bone material or a biocompatible bone substitute material (or a combination thereof) may be compressively engaged within the access channel to prevent the outflow, extrusion, or expulsion of the disc repair material, and to restore the mechanical integrity of the vertebral body. As described further below, a variation of the bone repair implant embodiment is one where the implanted bone repair includes a distal portion that serves as an intradiscal or intervertebral repair implant that functionally replaces the disc.

In some embodiments of the invention, a vertebral bone plate may be applied and fastened to the exposed surface of the host vertebral body, thereby covering the proximal end of the implanted bone repair device. The bone plate stabilizes the bone repair device in its host site, the former access channel, and supports the integrity of the host vertebral body. The bone plate, in an implementation of the method, is applied to the bone prior to the formation of an access channel, where it provides a base for a trajectory control sleeve which establishes an anatomically appropriate or prescribed path for a bone cutting device to form the channel. A prescribed path of trajectory of the transcorporal channel refers to a path that is planned by the surgical physician that is based on measurements or images of the vertebral site of the operation, and which are the basis for determining the precise angle which the channel needs to follow from the anterior surface to the target site within the endplate.

Embodiments of a trajectory control sleeve, one of the devices included in the inventive system, may be attached directly to an anterior vertebral surface, but are typically attached indirectly to the vertebral surface by way of temporary engagement to an implanted bone plate during the aspect of the procedure when the transcorporal channel is being formed by a bone cutting tool. The bone plate, thus is adapted to be compatible both with a trajectory control sleeve, when the channel is being formed with a prescribed trajectory, and also compatible with a bone repair device in that the repair device passes through the primary aperture of the bone plate.

The channel through a host vertebral body, as provided by embodiments of the invention, is oriented obliquely with respect to the plane of the targeted disc; it starts on the anterior surface of the host vertebral body and terminates at or near the end plate bone tissue of the vertebral body in the locale of the nucleus pulposus of the targeted disc. The formed channel then becomes the route through which the targeted disc is accessed for a procedure to remove or repair damaged tissue, and through which artificial disc substitute material can be introduced. On completion of such a procedure, the access channel may be filled with an embodiment of a bone repair device.

Figure 12A:
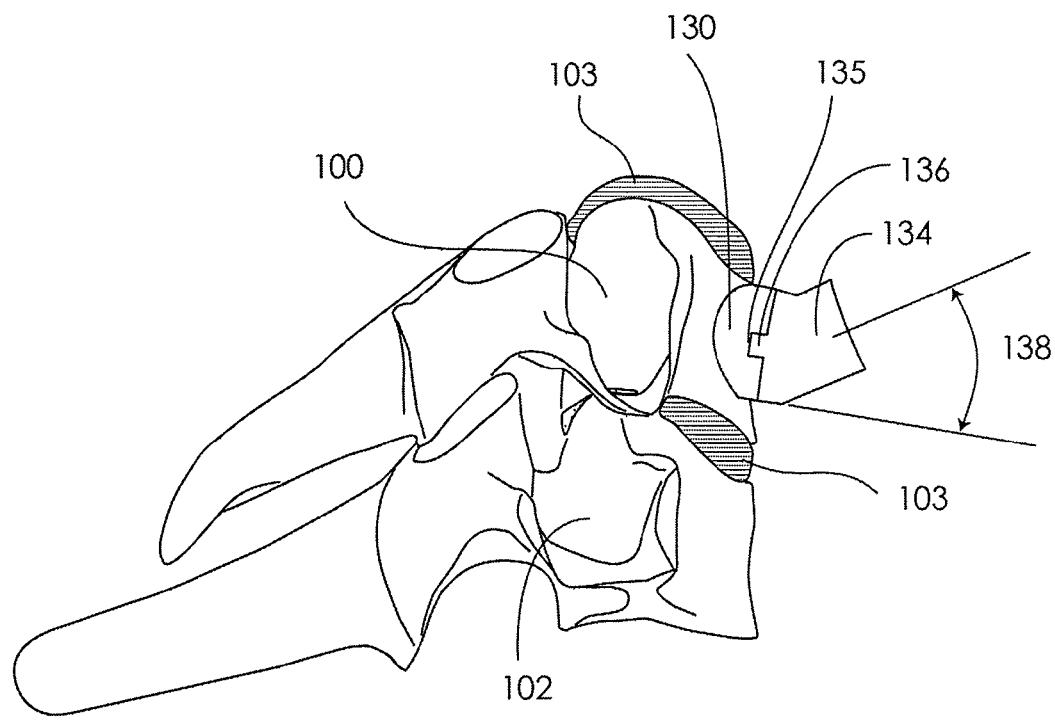
FIG. 12A is a side view of a vertebral body with a bone plate implanted on its anterior surface, and a trajectory control sleeve temporarily installed on the bone plate.
Figure 12B:
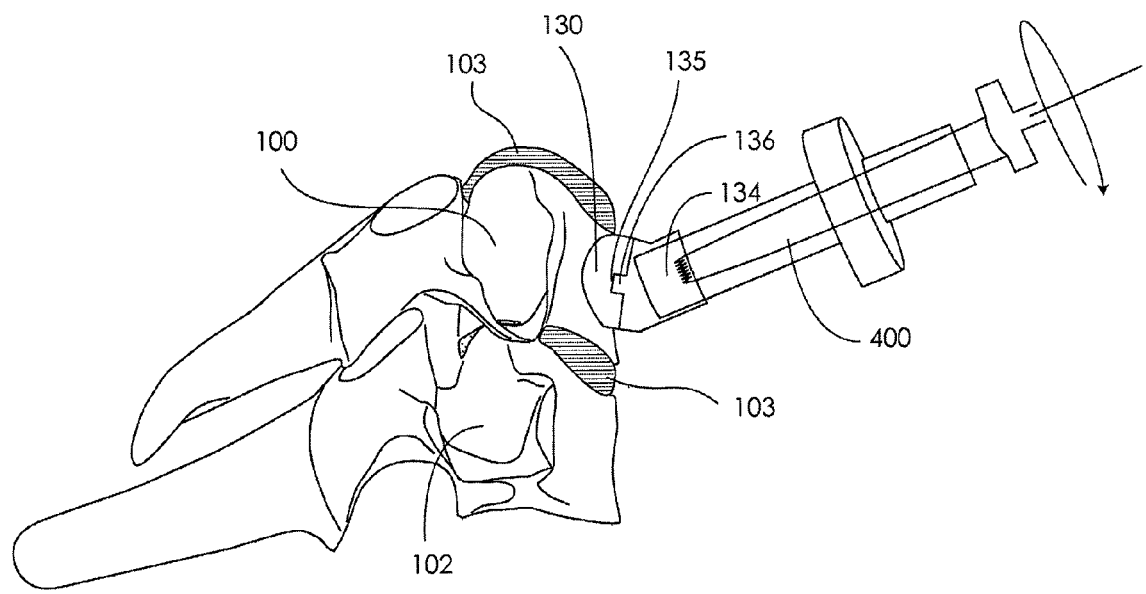
FIG. 12B is a side view of a vertebral body with a bone plate and a trajectory control sleeve as in FIG. 12A, with a bone cutting device engaged into the trajectory control sleeve, positioned to form a transcorporal access channel into the host vertebral body.

In some embodiments of the invention, the bone cutting tool that forms a transcorporal channel is a drill or a trephine, as exemplified by the embodiment depicted in FIG. 12B, which forms a straight channel. Bone repair devices appropriate for these channels are straight, as are embodiments depicted herein as examples of the invention. However, in other embodiments of this invention, a channel may be formed by a cutting tool affixed to a flexible shaft, or a cutting tool guided by a jig, as performed freehand, or by other methods known in the art, which form an arcuate channel. Methods may be applied, for example, as described in the U.S. patent application Ser. No. 10/968,867 of Carl et al. (Publication No. 2005/0267481, published Dec. 1, 2005). Aspects of the present invention, accordingly, include bone repair devices and systems that are arcuate or curvilinear, as are appropriate and complementary to arcuate transcorporal channels. Straight transcorporal channels and arcuate transcorporal channels each may have particular benefits or advantages, depending on particulars of the patient's spine, the vertebral body location within the spine, the elected site of transcorporal channel entry, and the instruments that are used in the procedure.

Some embodiments of the inventive method include creating a channel within a vertebral body and thereafter through the space of the nucleus pulposus of the adjacent disc, terminating at the end plate bone tissue of the vertebral body adjacent to the nucleus pulposus. The method may continue with the insertion of an intervertebral implant device through the channel, the distal end of the implant engaging the end plate bone tissue of the adjacent vertebral body to provide a load bearing and articulating surface that engages the adjacent vertebra so as to restore normal motion to the vertebral joint. Some embodiments of the intervertebral implant device are formed as a unitary device that includes a biocompatible material such as polyethylene, polyetheretherketone (PEEK), tantalum, or a titanium alloy. Other embodiments of the intervertebral implant device may be formed as device that includes two regions of at least partially distinct composition, the distal end of the device including a pliant or resilient material appropriate and compatible with disc tissue and the proximal portion of the device being appropriate and compatible with bone.

In some embodiments of the invention, some intervertebral void space resulting from the creation of the access channel may remain even after implantation of a bone repair device. Such void space may be filled with a bone substitute implant of synthetic or natural composition that prevents leakage of the artificial disc substance out of the normal confines of the disc space and further supports the structural integrity of the host vertebral body.

Some embodiments of the invention include a surgical system and related method for accessing and repairing, restoring or replacing degenerative disc tissue within the annulus fibrosis of an intervertebral disc. In this method, an access channel of a prescribed size and trajectory is created in a vertebral body, the channel having a prescribed point of entry on an exposed vertebral surface and having an exit on the end plate of the same vertebral body, the exit being located within the inner perimeter of the annulus fibrosis of the intervertebral disc. In some embodiments, the internal disc material is excised through the access channel, a substitute disc material is inserted into the intra-discal void and the access channel is repaired by the insertion of a bone repair implant, having a complimentary size, within the access channel.

Some embodiments of the invention include an implantable bone repair device having a lumen or internal channel connecting the proximal and distal ends of the implant, the lumen having a unidirectional valve. The lumen is configured to receive a filling element inserted there through for the purpose of conveying an injectable liquid phase disc replacement material into an internal disc volume, the volume being contained within the annulus fibrosis of the disc. The unidirectional valve is configured to allow the passage or penetration of the injection element therethrough and to provide a sealing means upon the removal of the injection device. This device is used in a method that includes creating an open channel in a vertebral body which starts on an exposed surface and is obliquely directed to a termination at the end plate, the terminus in the locale of the nucleus pulposus of the adjacent disc. The method continues with inserting a bone repair device with the internal channel or lumen into the transcorporal access channel, inserting a needle through the lumen of the bone repair device into the internal disc volume, and injecting a liquid or phase-changing disc substitute into the disc volume.

Alternative embodiments of the invention vary with respect to the site of entry of a channel into a vertebral body. For example, an alternative embodiment of the inventive method includes creating an open channel within or through a vertebral body from a trans-pedicular approach, the channel originating at the posterior aspect of a vertebral pedicle and terminating at or near the end plate of the vertebral body adjacent to the nucleus pulposus. Another alternative embodiment of the inventive method includes creating an open channel within or through a vertebral body from a posterior, lateral or posterolateral extra-pedicular approach, with the channel originating at the posterior-lateral aspect of a vertebral body and terminating at or near the end plate bone tissue adjacent to the nucleus pulposus.

Aspects and exemplary embodiments of the invention, as generally described above, are described further in the context of FIGS. 1-27, as follows below.

FIGS. 1A-1F are schematic cross-sectional views that storyboard a method for creating an transcorporal access channel within a vertebral body for accessing, repairing, replacing and/or restoring intervertebral disc tissue. The method continues with a repairing of the intervertebral access channel with a bone repair material, and affixing an implantable bone plate to the surface of the vertebral bone tissue to prevent migration of the bone repair implant out of the intervertebral access channel.

FIG. 1A show two adjacent vertebral bodies, a device-hosting vertebral body 100 and an adjacent vertebral body 102, and an intervertebral disc 103. A generally cylindrical intervertebral access channel 101 has been created within a vertebral body adjacent the disc to be repaired. The access channel has a point or site of entry 104 on the exposed surface of the vertebral body 100, and then penetrates the vertebral bone and exits through the vertebral end plate 105 at a site near the center of an intervertebral disc 103.

Figure 1B:
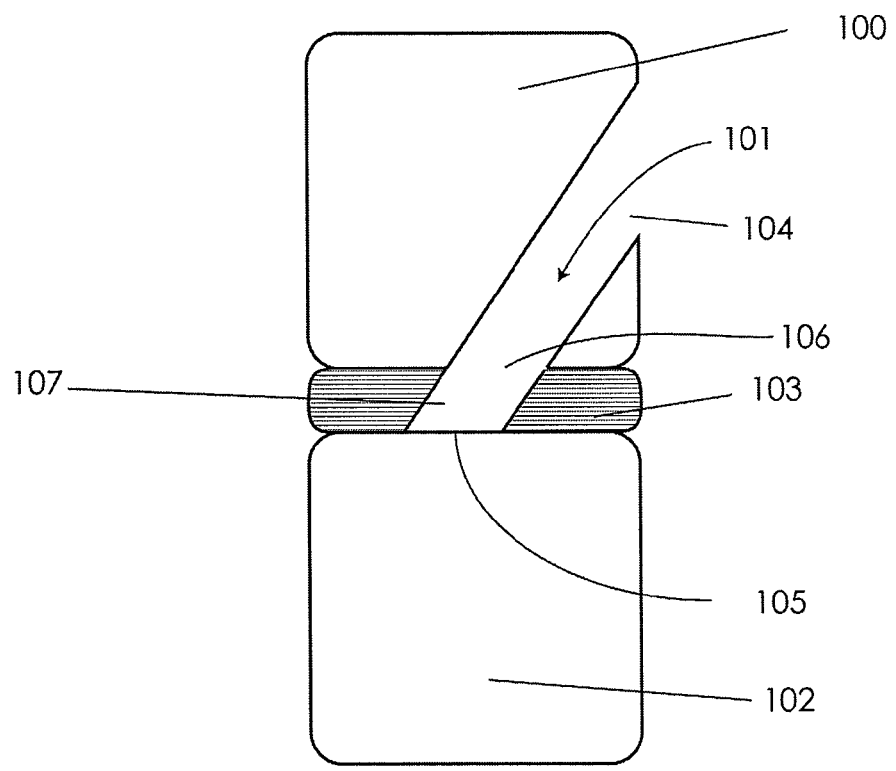

FIG. 1B shows a vacant internal volume 107 created within the central nucleus pulposus region of the intervertebral disc 103 that has been formed by surgically displacing or excising the nucleus pulposus tissue through the transcorporal access channel 101.

Figures 1C, 1D:
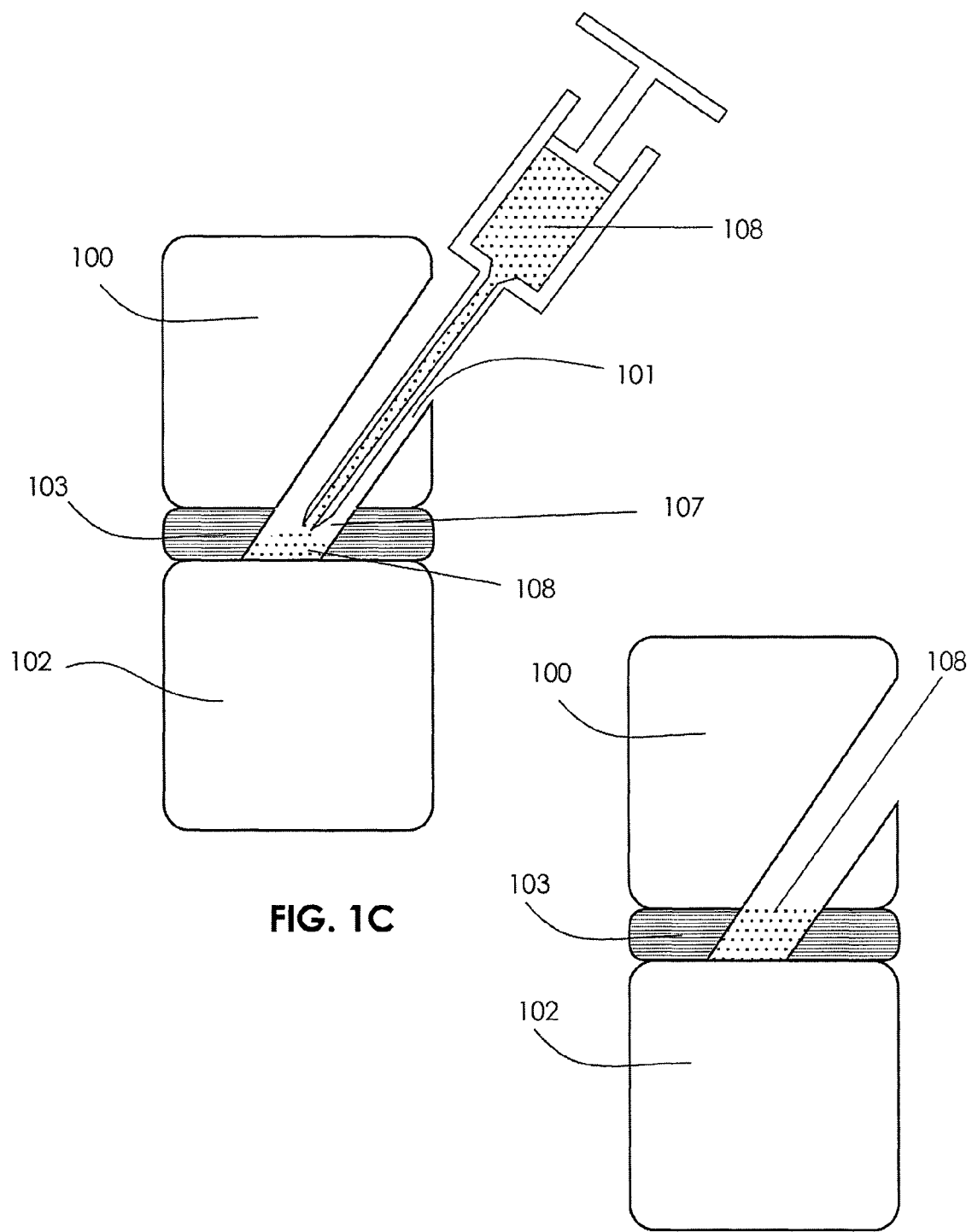

FIG. 1C shows an injection device introducing disc repair material 108 into the vacant internal disc volume 107 through the transcorporal access channel 101.

FIG. 1D shows the formerly vacant (FIG. 1C) internal disc volume now filled with the disc repair material 108.

Figure 1E:
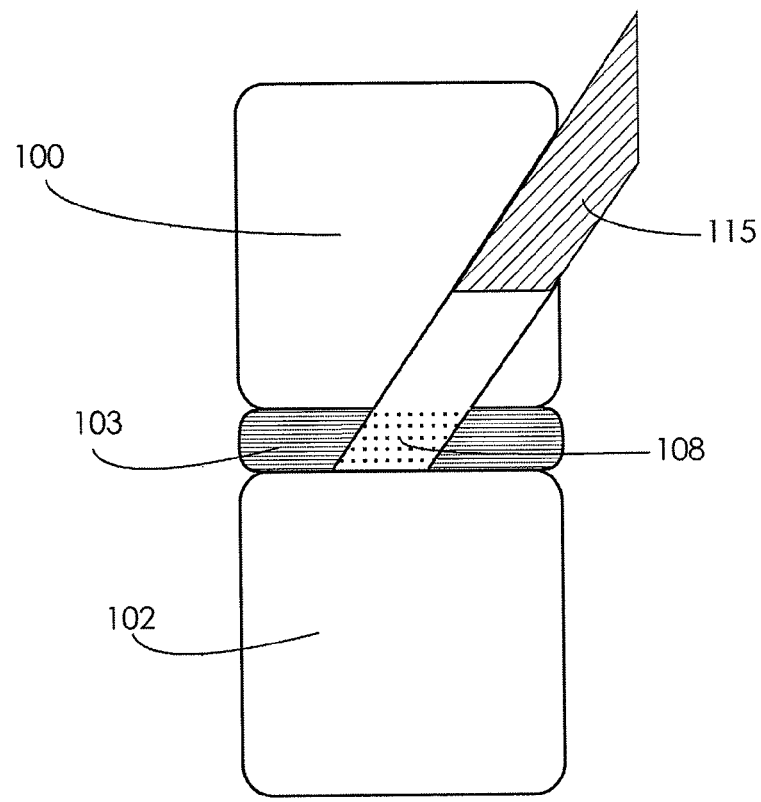

FIG. 1E shows the entry of a bone repair implant or device 115 into the transcorporal access channel 101.

Figure 1F:
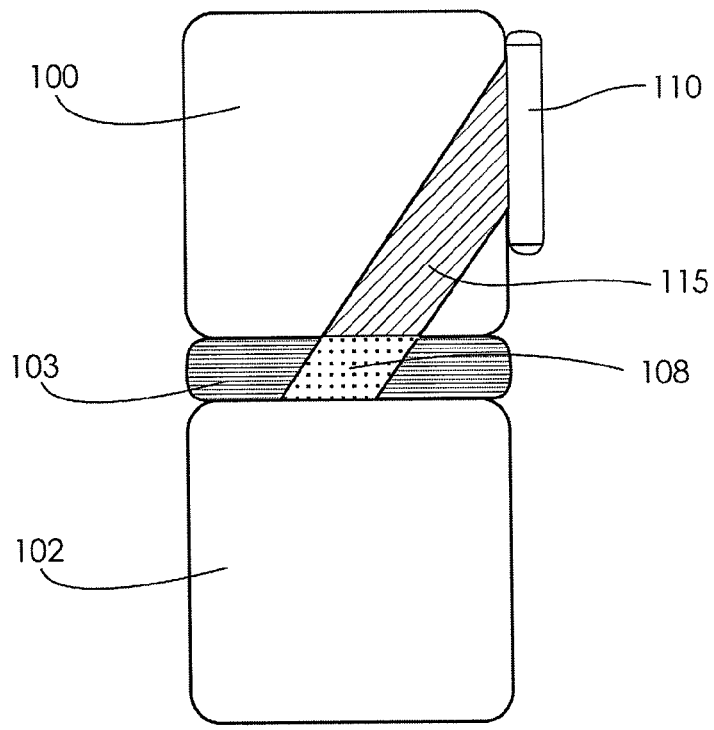

FIG. 1F shows a completed post surgical result of having repaired the intervertebral disc by implanting therein a disc repair material 108, having repaired the transcorporal access channel by inserting into it a bone repair device 115, and having secured the device 115 in the installed location by affixing a bone plate 110 to the exposed surface of the vertebral bone.

Figure 2:
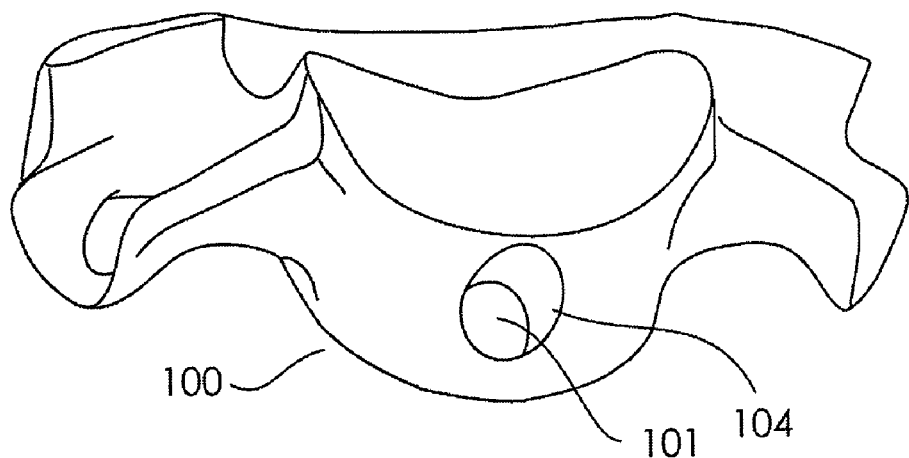
FIG. 2 is a perspective view of a vertebral body illustrating a transcorporal access channel from an anterior perspective.
Figure 3:
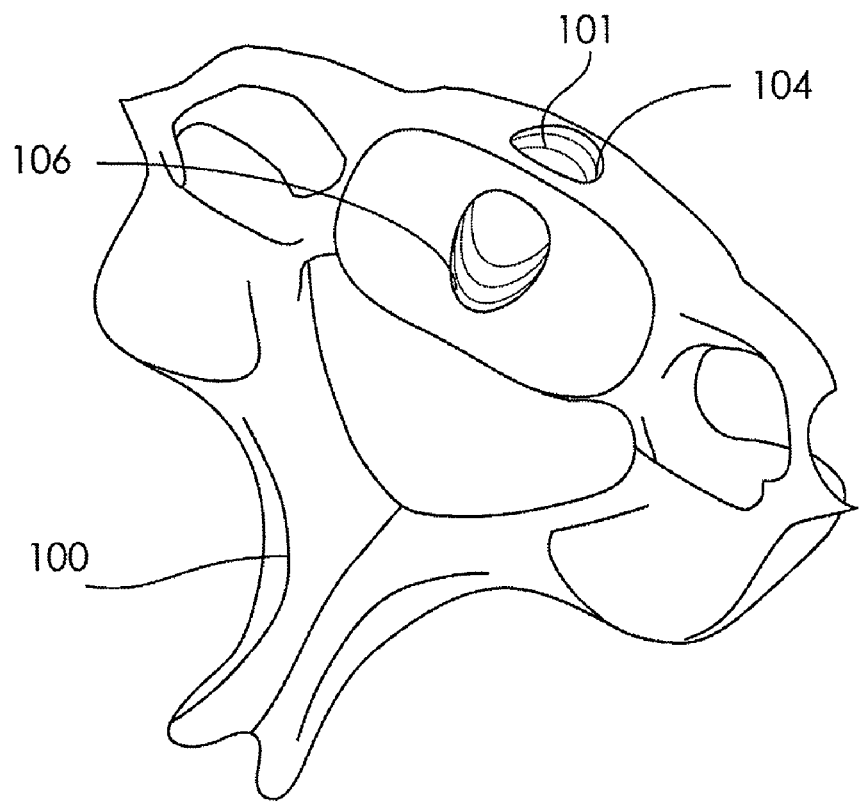
FIG. 3 is a perspective view of a vertebral body showing the exit point of the transcorporal access channel of FIG. 2 through the vertebral end plate.
Figure 4:
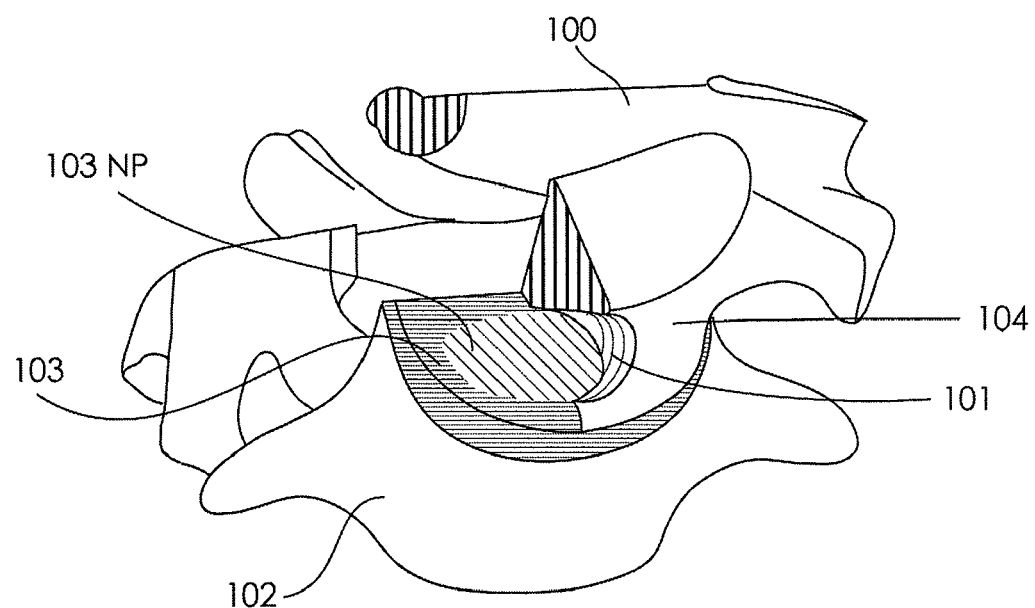
FIG. 4 is a cut away perspective view through a vertebral bone segment along the centerline of the transcorporal access channel, showing the access to nucleus pulposus of the intervertebral disc through the access channel.

FIGS. 2-5 show an embodiment of an transcorporal access channel 101 from various perspectives, and at various points in a surgical repair procedure. The channel 101 is generally cylindrical in form and has a point of entry 104 on the anterior surface of vertebral body 100 and a point of exit 106 on the vertebral end plate thereby providing unrestricted access to the internal nucleus pulposus portion 103np of the intervertebral disc 103 through the access channel. FIG. 2 is a perspective view of a vertebral body 100 showing a transcorporal access channel 101 from an anterior perspective. FIG. 3 is a perspective view of a vertebral body showing the exit point 106 of the transcorporal access channel of FIG. 2 through the vertebral end plate 105. FIG. 4 is a perspective view that includes a cut away view through a vertebral body 100 segment along the centerline of the transcorporal access channel 101, showing the access to nucleus pulposus 103np of the intervertebral disc through the access channel.

Figure 5:
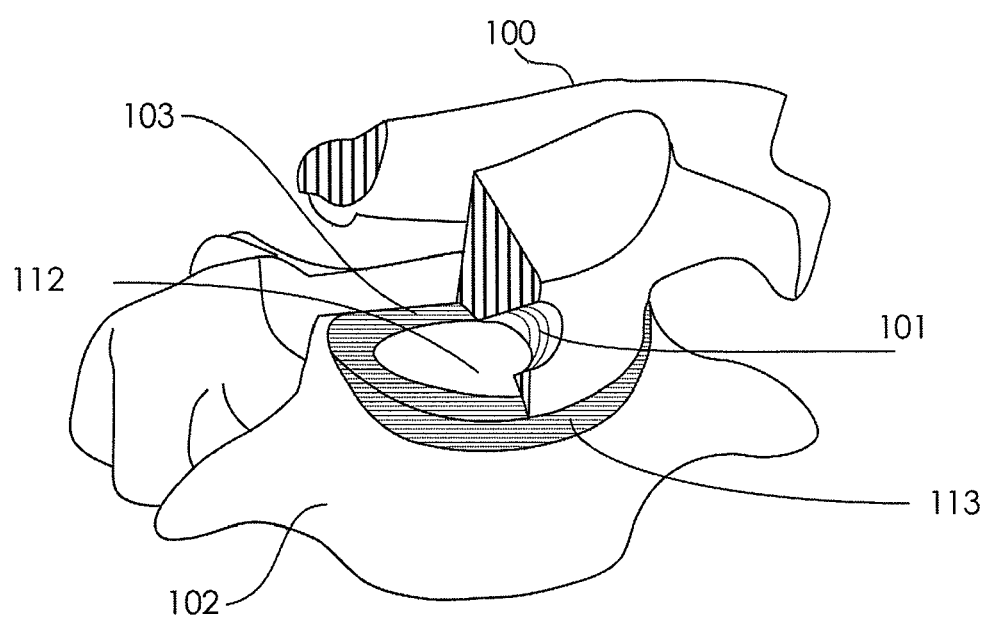
FIG. 5 is a perspective view that includes a cut away view through a vertebral bone segment along the centerline of the transcorporal access channel and illustrating the remaining annulus fibrosis of the intervertebral disc after the nucleus pulposus has been excised.

FIG. 5 is similar to FIG. 4, but focuses attention on an internal void 112 created within an intervertebral disc by a surgical procedure operated within the space provided by the access channel 101, in which the nucleus pulposus of the disc has been displaced or excised. The confinement of the procedure within the access channel has precluded the penetration or compromise the annulus fibrosis 113 of the intervertebral disc 103.

Figure 6:
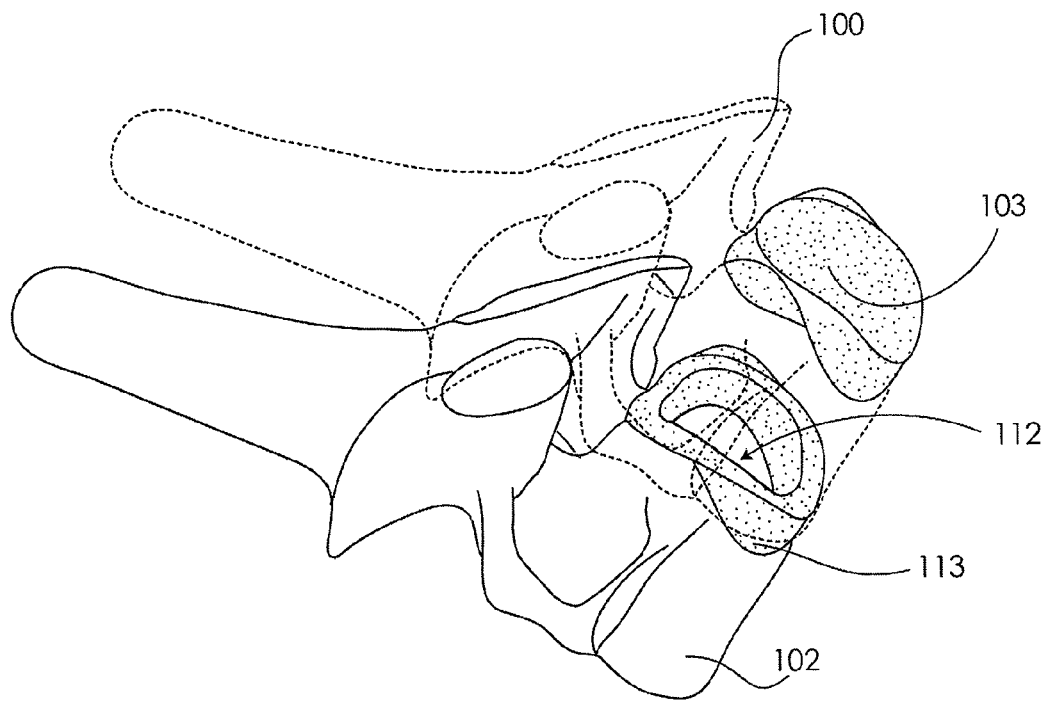
FIG. 6 is a lateral perspective view of adjacent vertebral bodies and the annulus fibrosis of the intervertebral disc after the nucleus pulposus has been excised.

FIG. 6 is a lateral perspective view of adjacent vertebral bodies (a device hosting vertebral body 100, shown transparently by dotted outline, and an adjacent vertebral body 102) and the annulus fibrosis 113 of an intervertebral disc remnant after its nucleus pulposus has been excised. An internal void 112 has been created and is confined within an intact annulus fibrosis 113af of the intervertebral disc.

Figure 7:
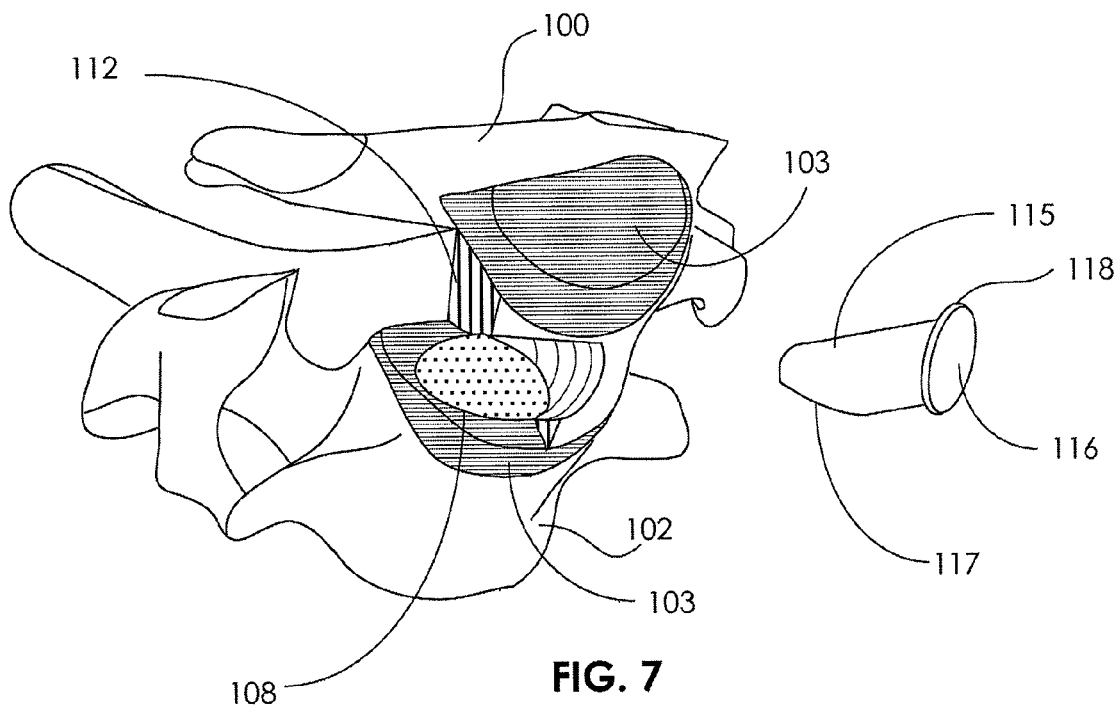
FIG. 7 is a perspective view of adjacent vertebral bodies with a cut away central focus on showing the nucleus pulposus volume of the intervertebral disc filled with a substitute disc material and the transcorporal access channel bone repair implant in the pre-installation position.

FIG. 7 is a perspective view of adjacent vertebral bodies 100 and 102 on either side of a repaired disc 103. The central portion of the figure includes a cut away of a portion of a vertebral body that allows a view of the repaired intervertebral disc, wherein the internal void 112 (FIG. 6) within the annulus fibrosis 113 of a disc has been replaced with a substitute disc material 108. FIG. 7 further shows a vertebral bone repair implant 115 embodiment suspended in space, but directed toward its host or installation site. Bone repair device 115 has a distal end 117 disposed to be generally meet the plane of the vertebral end plate 105 when implanted in its host site, and a proximal end 116 disposed to be generally proximal to the anterior surface of the vertebral body 100 when in the final installed position. The proximal end of bone repair device 115 may have an abutment 118 disposed to engage the anterior surface of the host vertebral body so as to prevent its insertion beyond the prescribed depth within the host vertebral body.

In various embodiments of the invention, the bone repair implant may include particular osteointegrative features such as those provided in U.S. Patent Application No. 60/972,192 of Lowry et al., as filed on Sep. 13, 2008. Examples of osteointegrative features include the external surface of the devises having at least a portion of which is porous enough for native bone ingrowth, and incorporating osteogenic agents into the matrix of the bone repair device. Inclusion of a bone cell preparation within the device, as described further below, is also a major osteointegrative feature, as such bone cells can migrate into the host site, and knit together host and grafted bone.

Figure 8:
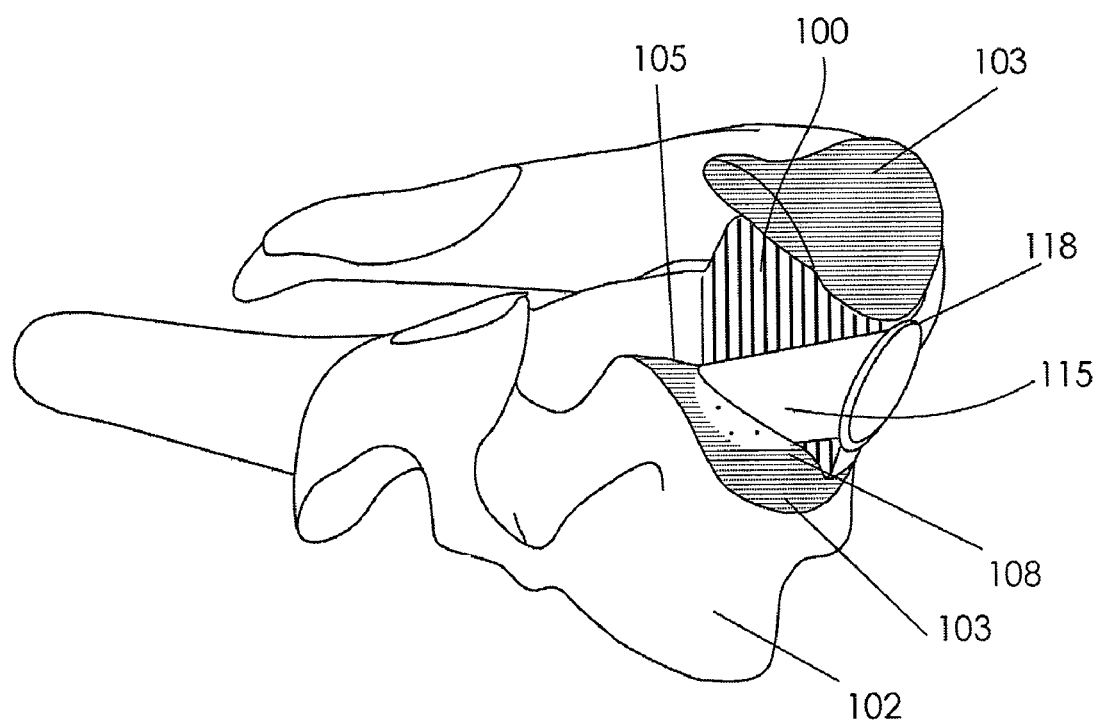
FIG. 8 is a perspective view of adjacent vertebral bodies showing the nucleus pulposus volume of the intervertebral disc filled with a substitute disc material and the transcorporal access channel bone repair implant in the installed position.

FIG. 8 is a perspective view of adjacent vertebral bodies 100 and 102 with a cutaway central portion of the superior and host vertebral body 100 that has been operated on, showing the nucleus pulposus volume of the intervertebral disc 103 filled with a substitute disc material 108 and the formally open transcorporal access channel now occupied by the installed bone repair implant 115 embodiment. Below the now repaired disc 100 is an adjacent and intact vertebral body 100. The abutment 118 of the bone repair implant 115 can be seen flush against the surface of the host vertebral body. The distal end of bone repair implant 115 (not visible) can be understood to meet the end plate 105 of the host vertebral body. An intact disc 103 can be seen on the superior aspect of the host vertebral body.

Figure 9:
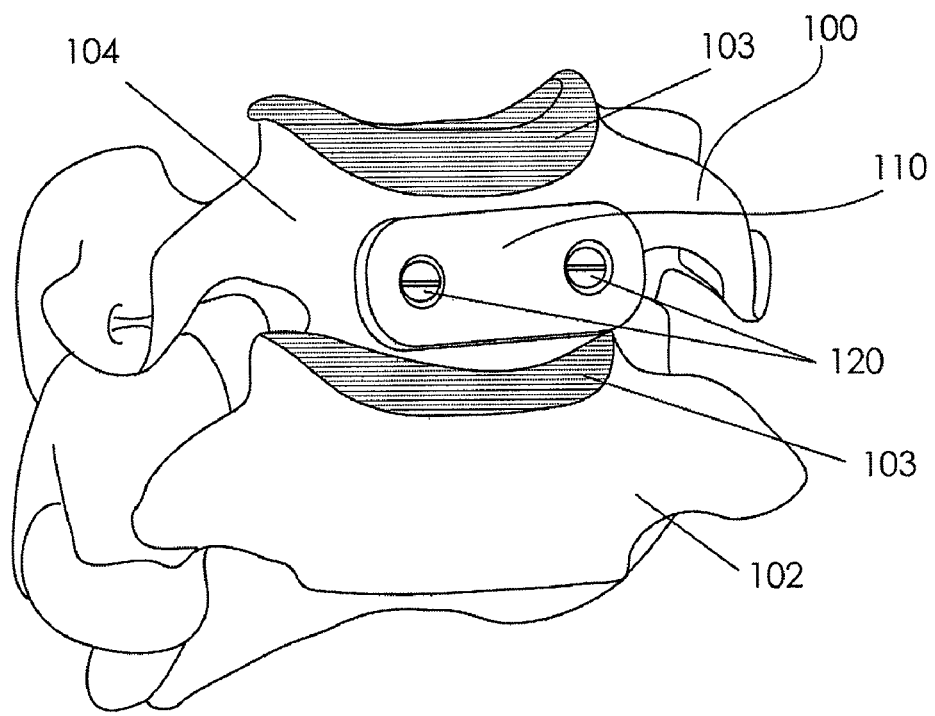
FIG. 9 is an anterior perspective of a vertebral body showing a bone plate in the installed position, covering the proximal end of the transcorporal repair implant device (not visible).

FIG. 9 shows a bone plate 110 embodiment permanently affixed to the anterior surface of a host vertebral body 100 by one or more bone screws 120, the bone plate engaging the proximal end of the bone implant 118 (not visible here, but shown in FIG. 8) so as to prevent migration of the implant out of the access channel. Discs 103 lie above and below the superior host vertebral body; an adjacent intact vertebral body 100 lies inferior to the host vertebral body.

Figure 10:
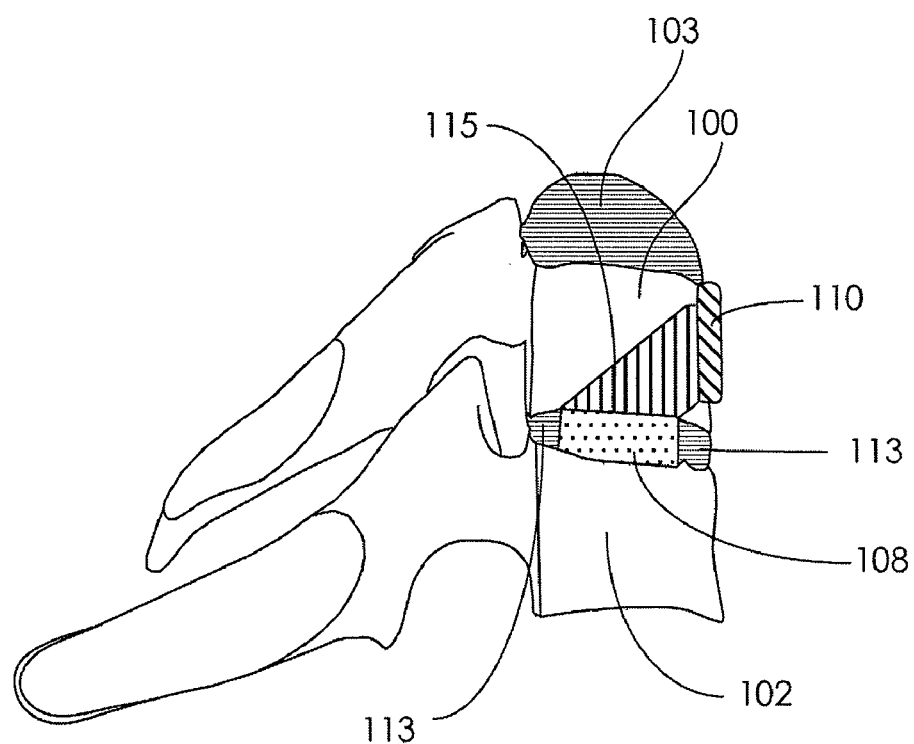
FIG. 10 is a cross-section side view of two adjacent vertebral bodies showing the completed disc repair, illustrating the intact annulus fibrosis of the intervertebral disc, the substitute disc material contained therein, the access channel bone repair implant in the fully installed position and the bone plate installed on the vertebral body.

FIG. 10 is a cross sectional side view of adjacent vertebral bodies 100 and 102, a repaired intervertebral disc 103, the disc having an intact annulus fibrosis 113 and a substitute disc material 108 contained therein. The formerly open transcorporal access channel has been repaired with an implanted bone repair device 115 and a bone plate 110 fastened to the vertebral body over the bone repair device to prevent its migration, and to assure the optimal mechanical integrity of the post-operative vertebral body.

Some embodiments of the invention are directed toward the implantation of devices through a host vertebral body that include a disc-replacing portion with a distal surface that is articulatable against the end plate of the adjacent vertebral body. Such articulatable surfaces are hard and smooth. In some embodiments, these devices are implanted singly in a host vertebral body, and in other embodiments, these devices are implanted as a side-by-side dual set, hosted by dual channels within a vertebral body. The dual channel (dual devices) approach differs from the typical embodiment used when surgical access to a disc is the primary purpose of a procedure; these embodiments typically make use of a single channel with the implantation of a single repair device. In embodiments of the invention that include the implantation of an articulating disc replacement, dual channels (and dual implanted devices) may provide particular benefit with regard to maintaining posture and symmetrical load bearing within the spine.

Figure 11:
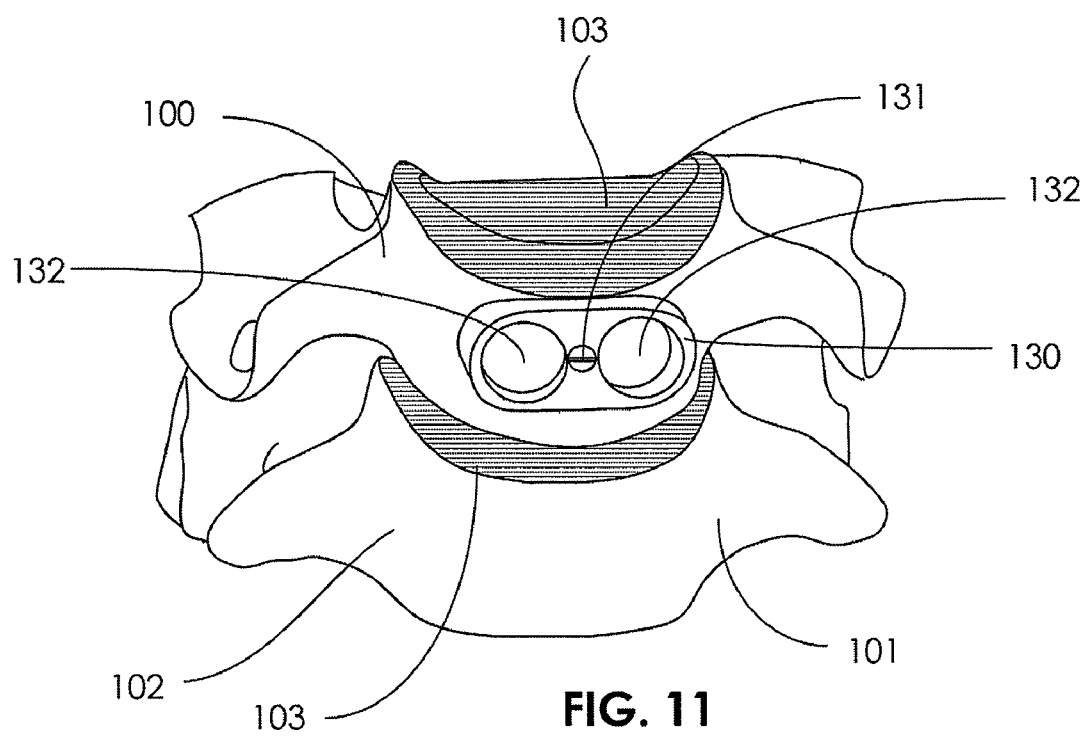
FIG. 11 is an anterior view of a vertebral body with a bone plate implanted on its anterior surface, with two integral tissue access ports visible on the bone plate.

FIG. 11 is a perspective view of adjacent vertebral bodies 100 and 102, and intervertebral discs 103 lying above and below the superior vertebral body 100 that is now host to an embodiment of an implanted bone plate 110. The bone plate 130 is attached to the exposed surface of a host vertebral 100 by one or more bone screws 131 in a manner so as to symmetrically locate the bone access ports 132 relative to the medial centerline of the vertebra, thereby establishing a point of entry for a tool such as bone cutting device at the bone surface.

FIG. 12A is a side view of a spinal section having an embodiment of a bone plate 110 affixed to the anterior surface of a vertebral body 100 and an embodiment trajectory control sleeve or cutting tool holder 134 positively engaging the bone plate 110. Bone plate 100 and trajectory control sleeve 134 have complimentary orientation control features 135 (on the bone plate) and 136 (on the trajectory control sleeve). These features are configured to establish a desired angle 138 of penetration for a bone cutting device such as a drill from a point of entry 137 (in FIG. 11) and into the vertebral bone so as to assure that the point of exit of the drill at the vertebral end plate is adjacent to the annulus fibrosis of the intervertebral disc. These complementary features, while generally fixed on any given device (bone plate or trajectory control sleeve), may be varied from device-to-device, either on one or both of the complementary devices, in order to form a desired angle. Further, in some embodiments, one or both of the features of the complementary devices may be configured such that the angle of engagement is adjustable. FIG. 12B is a side view of a vertebral body with a bone plate and a trajectory control sleeve (as in FIG. 12A) with a bone cutting device 400 engaged into the trajectory control sleeve, positioned to form a transcorporal access channel into the host vertebral body.

Figure 13:
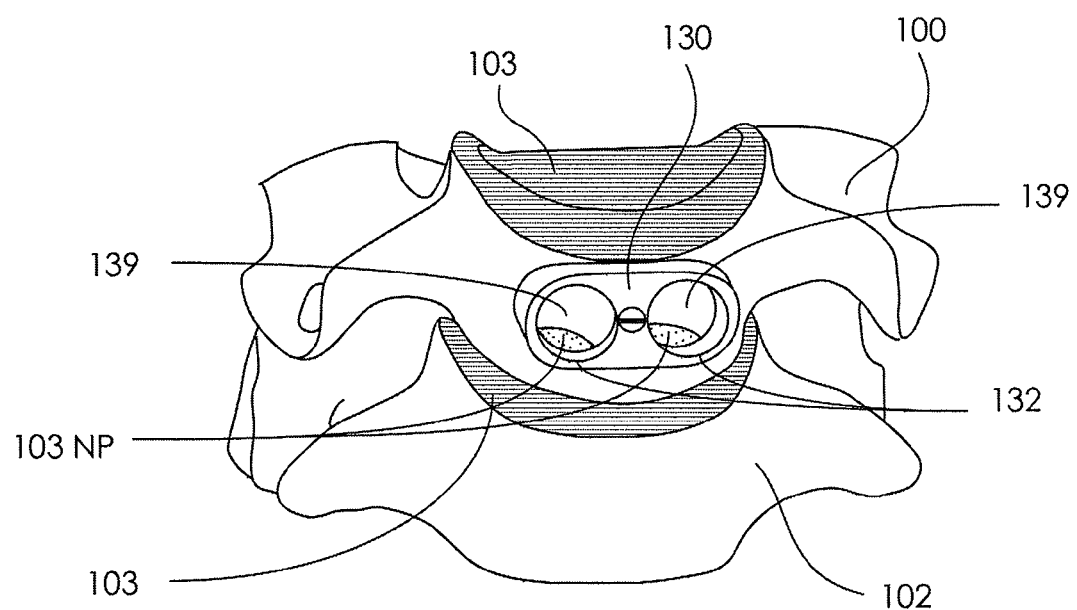
FIG. 13 is an anterior view of a vertebral body with a bone plate implanted on its surface, and with integral tissue access ports that have been used to provide access to a cutting tool guided by a trajectory control sleeve to form transcorporal access channels.

FIG. 13 is an anterior perspective view of a vertebral body 100 that shows two substantially parallel transcorporal access channels 139 through the vertebral body. A nucleus pulposus 103NP portion of an intervertebral disc 103 is exposed through the access channels that are framed by bone plate 110. The channels 139 have been formed with a cutting device whose path was directed by a trajectory control sleeve or cutting tool holder 134 (see FIG. 12) which has since been removed.

Figure 14:
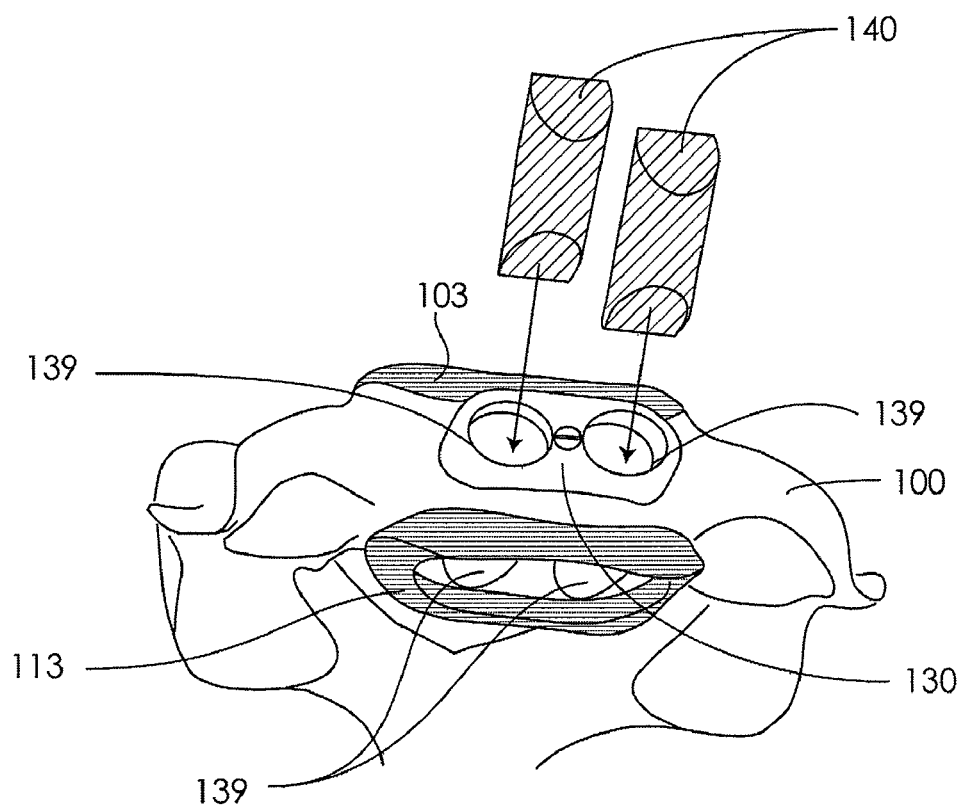
FIG. 14 shows a pair of interbody disc implant devices schematically suspended in air aligned and aligned for entry into prepared access channels through an implanted bone plate.

FIG. 14 shows a pair of intra-discal implant 140 embodiments schematically positioned in an alignment directed toward the anterior openings of the transcorporal access channels 139 within the bone plate 110 implanted in vertebral body 100. Intra-discal implants or repair device embodiments are similar to bone repair device (generally labeled 115) embodiments as described above and as depicted in FIGS. 7 and 8, however the intra-discal implants (generally labeled 140) have further structure and function such that, when implanted, they extend beyond the bone plate and occupy space that replaces an excised nucleus pulposus portion of an intervertebral disc. As will be described below and as comparatively depicted in FIGS. 16 and 17, intra-discal implants or repair devices may be of a unitary construction and composition 140A or they may be of a composite construction 140B, including at least two different portions.

Figure 15:
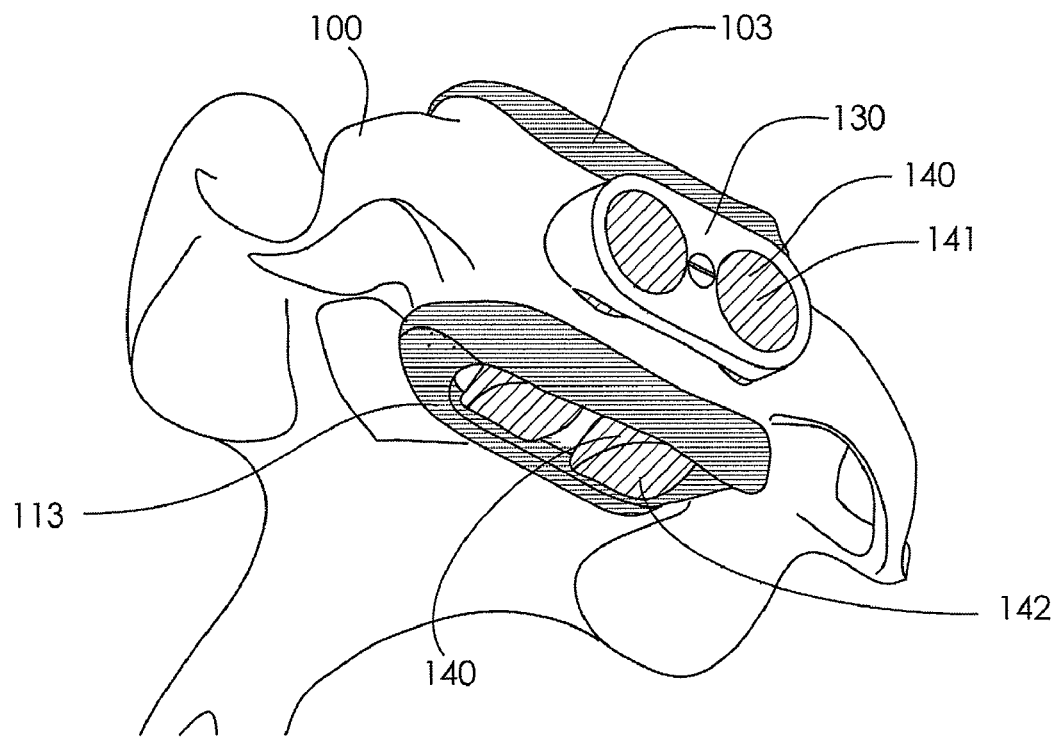
FIG. 15 is an illustration of two interbody repair devices in their fully installed position with the distal ends protruding past the end plate into the interdiscal space within the annulus fibrosis.

FIG. 15 shows embodiments of two intra-discal implants 140A in their fully inserted position in a host vertebral body 100. The implants have a proximal end 141 that engages the bone plate 110 in a manner that controls the depth of penetration of the distal end 142 into the intervertebral disc space. FIG. 15 further illustrates that the intra-discal implants 140A are contained within an intact annulus fibrosis 113 of the remnant disc.

A function of embodiments of intradisc repair implant 140 (FIGS. 16 and 17) is to replace degenerated native disc material, to restore articulating motion between the adjacent vertebral segments, and to restore disc height while preserving the annulus fibrosis of the disc and substantially all of the native vertebral end plate tissue. Further, the mechanical integrity of the vertebral body transgressed by the access channel is restored by the insertion of the bone repair implant, the implant device 140 thus facilitates its own osteointegration with the native bone tissue of the host vertebral body 100 during the healing process.

Figure 16:
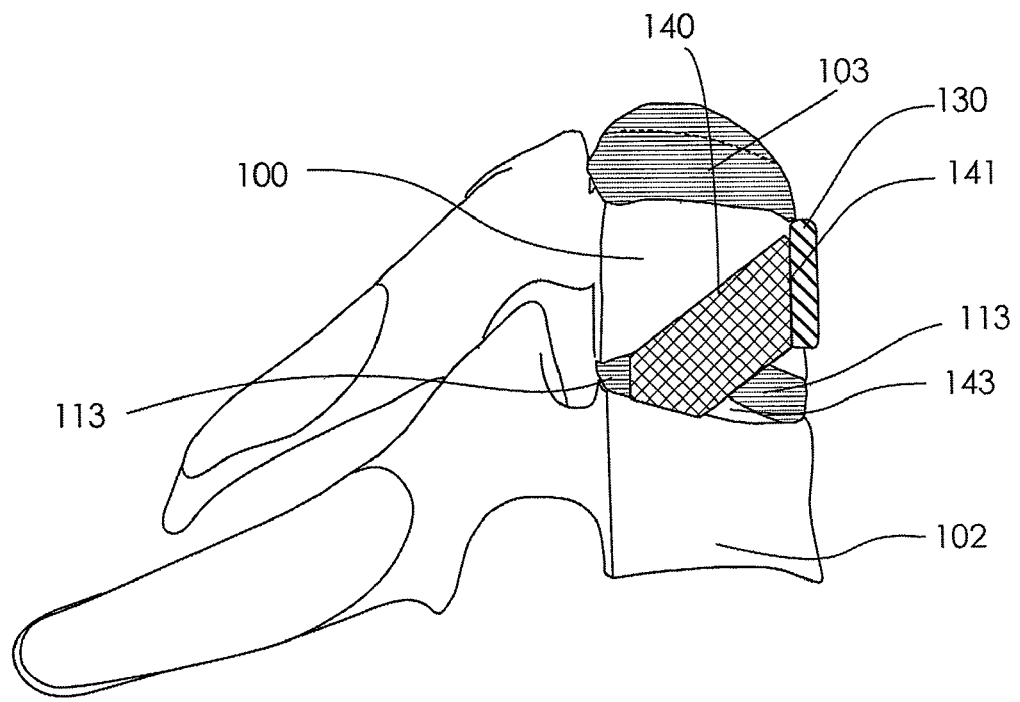
FIG. 16 is a cross section view of two adjacent vertebrae, showing the intact annulus fibrosis of the intervertebral disc and a unitary interbody repair device in the fully installed position.
Figure 17:
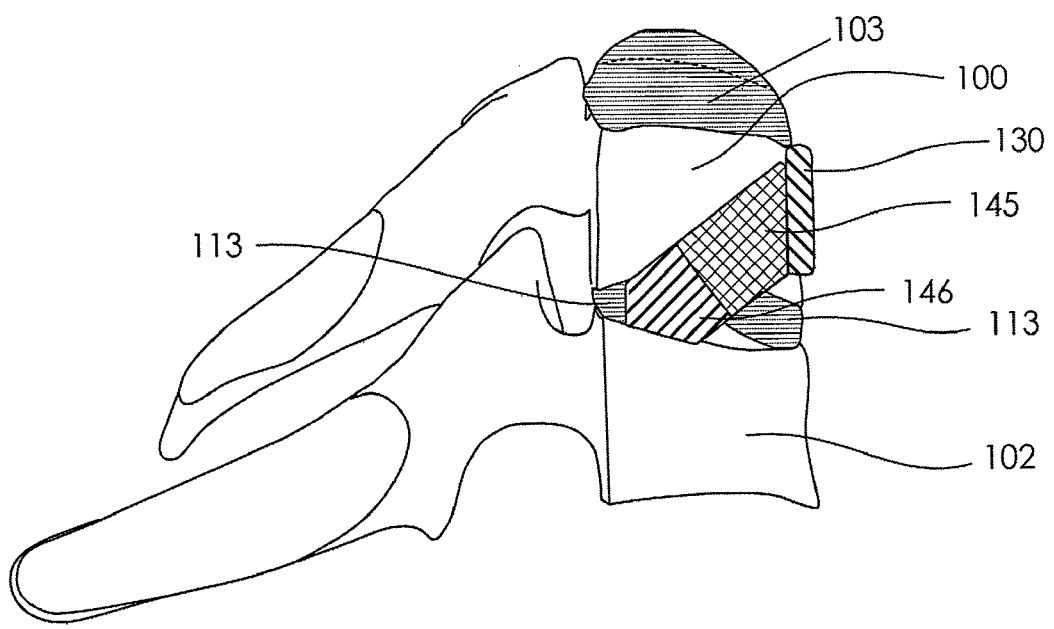
FIG. 17 is a cross section view of two adjacent vertebrae, showing the intact annulus fibrosis of the intervertebral disc and a composite interbody repair device in its fully installed position with the pliant disc substitute material being in intimate contact with the end plate of the adjacent vertebra and the bone repair material in intimate contact with the cancellous bone tissue within the transcorporal access channel.

FIG. 16 is a cross sectional view of two adjacent vertebrae 100 and 102 with an embodiment of a unitary intra-disc repair implant 140A inserted through a transcorporal access channel within a host vertebral body 100. The device 140A is implanted in such a manner so as to assure intimate or abutting contact between the distal end 142 of the device and the end plate bone tissue 105 of the adjacent (non-hosting) vertebral body 102. The site of contact occurs within bounds of the intact annulus fibrosis of the intervertebral disc 113, the nucleus pulposus having been removed. The proximal end 147 of the intra-disc repair implant 140A device may lockably engage the bone plate 110 or may be retained in place by the attachment of a complimentary bone plate device. FIG. 17 shows an alternate embodiment of a repair implant, this embodiment being an intra-disc repair device 140B used as described in conjunction with FIG. 16. This embodiment of the implantable device is formed as a construct of two materials; the proximal portion 145 includes a biocompatible bone repair material so as to promote bone in-growth therein and the distal portion 146 includes a pliant material with characteristics comparable to those of natural disc tissue so as to improve shock absorption and enhance relative motion between the adjacent vertebral bodies 100 and 102. As described further below, embodiments of the proximal portion 145 of the device may also include bone cell preparations.

In various embodiments of the invention, the bone repair implant may include particular osteointegrative features such as those provided in U.S. Patent Application No. 60/972,192 of Lowry et al., as filed on Sep. 13, 2008, which is incorporated into the present application in its entirety by this reference. That application described in detail the use of a preparation of the patient's own bone within a porous cage like device that ultimately integrates into the host vertebral body. These use of a trephine to form a channel is shown in FIG. of 30 of application 60/972,192, and various views of embodiments of the porous cage device and the method of implanting it are shown in FIGS. 31-37.

Embodiments of the porous cage device, or the porous cage proximal portion of the device and aspects of its preparation and implantation will now be described briefly.

Implantation of the patient's own bone tissue (an autologous graft) is a generally advantageous approach to repairing bone, as autologous grafting typically yields high success rates and a low rate of surgical complications. Accordingly, some embodiments of the invention include using core bone tissue harvested from the forming of the vertebral access channel, and implanting the plug, intact, in the form of bone repair graft. An advantage to recovering and making use of bone derived from the channel includes the absence of a need to harvest bone from a second site. Embodiments of the invention, however, do include harvesting bone from secondary sites on the patient, such as the iliac crest, as may be appropriate in the practice of the invention under some circumstances. In some embodiments, for example, it may be advantageous to supplement bone derived from the access channel with bone from other sites. In still other embodiments, under various clinical circumstances, it may be appropriate to make use of bone from donor individuals. Bone from other autologous sites or other donor individuals may be used as a repair device in the form of an appropriately formed plug, or bone may be fragmented or morselized, and packaged as a solid plug, or bone may be included as a preparation provided in a porous cage, as described further below.

Some embodiments of methods provided make use of a trephine type bone cutting system, as noted above. With a trephine bone cutting system, the external diameter of the bone tissue core is about equal to the internal diameter of the trephine device, while the internal diameter of the access channel is about equal to the external diameter of the device. Thus, a trephine-derived bone plug from forming the access channel provides an appropriately-sized piece to be inserted into the channel for repair and healing, but does not necessarily make intimate contact with the inside surface of the channel due to the width of the kerf created by the trephine.

Optimal healing and recovery from implantation of bone material into an access channel occurs when there is an intimate or compressive engagement of the graft material with the vertebral bone tissue (substantially cancellous bone), as this intimate association provides for rapid blood profusion and bone healing while providing mechanical support during healing. Accordingly, an embodiment of the bone repair device provided herein includes a device with bone tissue inside a porous cage, as described in detail below.

The porosity of the cage is a particularly advantageous feature for allowing cell to cell contact through the boundary of the device. To some degree, it may also allow cell migration, however the most advantageous factor in promoting rapid healing is cell to cell contact that initiates sites of tissue unification, which can then spread, stabilize a healing zone around the graft or bone repair device, and ultimately lead to effective fusion and integration of the graft within the host vertebral body.

A porous cage, as provided by this invention, also has a compressibility, such that when the contents of the cage are subject to a compressive force, however transient and minimal, blood or plasma and bone cells that are present in the harvested cancellous bone are forced outward into the environment within and around the access channel site. Extrusion of biological fluid in this manner, advantageously packs bone tissue closer together within the cage, and bathes the periphery of the graft and the host-graft intersectional zone with a medium that is optimal for exchange of dissolved gas and nutrients that are critical in the initial stages of healing. Some embodiments of the invention include bathing the bone tissue preparation in a supportive liquid medium before implantation. Such bathing may occur prior to placing the bone tissue preparation in the porous cage and/or after placing the preparation in the cage. The liquid medium may be any appropriate cell culture medium, and may be further supplemented with biological agents, such as osteogenic agents or other growth factors.

Embodiments of the implantable porous cage bone repair device, as provided herein, encapsulate the bone tissue contained therein, and provide mechanical stability to the access channel during healing. These embodiments compensate for the volumetric loss associated with the bone cutting process of the trephine and promote contact between the bone volume within the device and the surrounding vertebral bone tissue. The device, as a whole, and like other bone repair embodiments provided, cooperates with the implanted bone plate so that the orientation and penetration depth of the implant device within the access channel may be controlled. These forms of control assure that the device does not over-penetrate through the channel, thereby compressing the dura mater or neural elements within the vertebra, and assuring that the implanted device cannot migrate in an anterior direction out of the access channel.

In various alternate embodiments of the invention, a bone repair implant or an intradisc repair device may be held in place with bone cement, by a press-fit with the bone and/or by screwing the implant into the bone. These methods may be used independently or in conjunction with a bone plate 110 described above. Embodiments of the bone plate may be constructed from a biocompatible polymer, a biocompatible metal, a biocompatible ceramic and/or a bioabsorbable material. A biologically-absorbable or partially-absorbable bone plate is particularly compatible in the context of embodiments of the method in which the bone repair device is osteointegrative, as for example, when it includes bone tissue that ultimately fuses and/or integrates with bone of the host site. In these instances, once integrated, a bone plate may serve no substantially beneficial purpose, and restoration of the surgical site to a near-native configuration may be beneficially served by the absorption of bone plate material. In some embodiments of the inventive system and methods of operating the system, the bone plate may be temporarily in place during a spinal procedure, and it may be removed, for example, after an intervertebral channel has been formed, or after a spinal repair device has been implanted.

An alternate embodiment of the invention will now described in which disc repair is not performed by implantation of a preformed solid implant such the exemplary devices 140A or 140B as described above, but rather, repair is effected by injection of a flowable material that solidifies into a supporting structure. As previously described and as FIGS. 2, 3, and 4 show, an transcorporal access channel 101 created through a vertebral body between an exposed surface on the vertebral body and the end plate bone tissue of the vertebra and FIGS. 5 and 6 show the formation of an intra-disc void. In the present alternative embodiment of the invention (FIGS. 18-27), thereafter a bone repair implant having an internal filling channel or lumen is inserted into the transcorporal access channel and the intra-disc void is filled with a fluidic or flowable material, such as, by way of example, a liquid, a liquid-to-solid phase-changing material, a settable liquid, a gel, a suspension, or a slurry by means of a fluid injection device such as a syringe needle, the injection device being inserted into the intra-disc void through a filling channel within the bone repair implant device.

Figure 18:
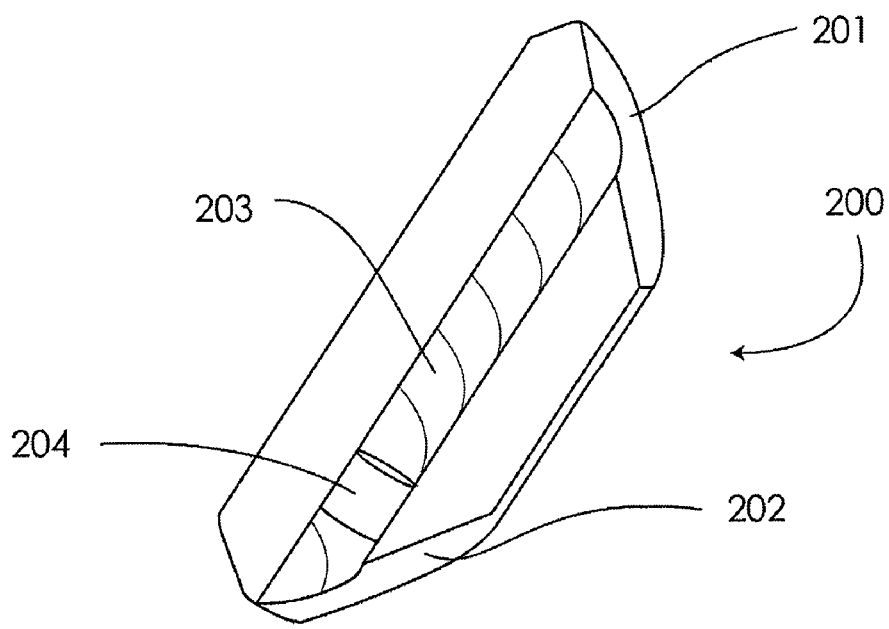
FIG. 18 is a cross section view of an interbody repair device the device having a central filling channel therethrough and a fluid backflow prevention device within the channel.
Figure 19:
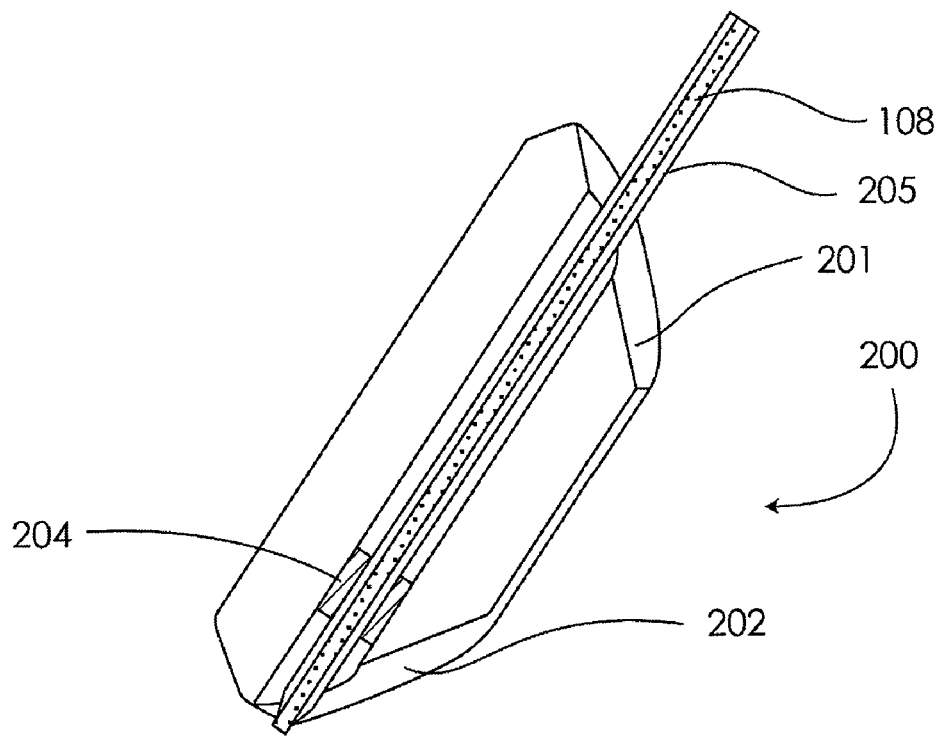
FIG. 19 is a cross section view of an interbody repair device with a fluid injection device within the central filling channel and penetrating through the backflow prevention device.
Figure 20:
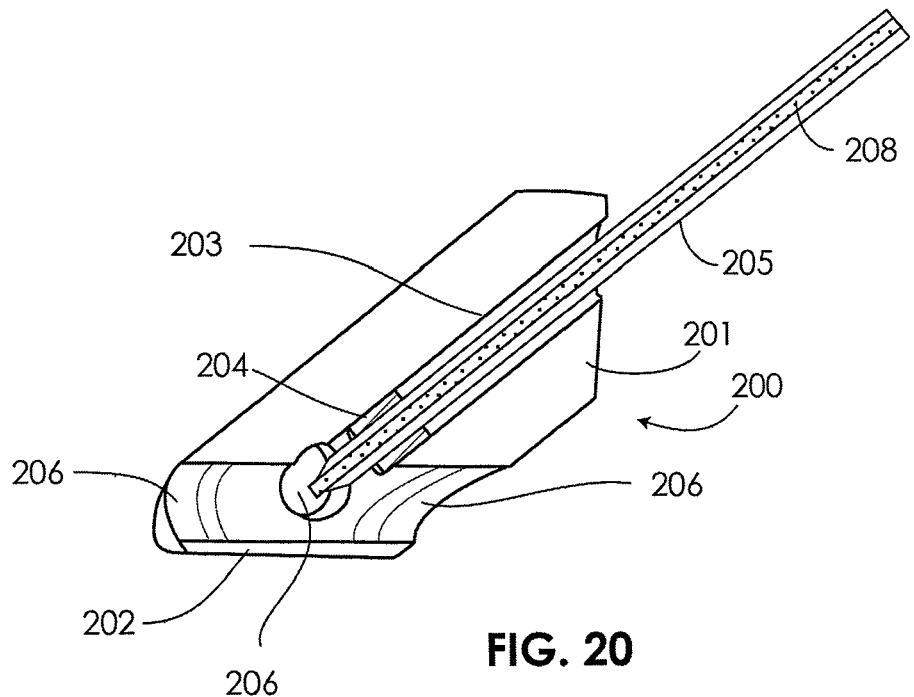
FIG. 20 is a cross section view of an interbody repair device having a fluid egress path located radially around distal end of the repair device.
Figure 21A:
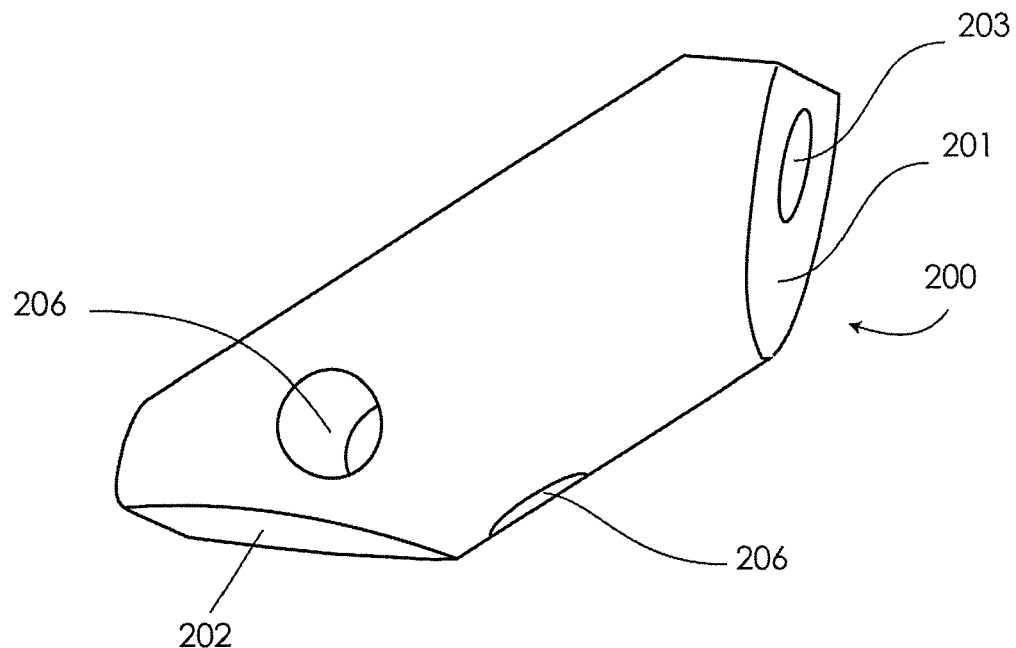
FIG. 21A is a perspective view of an interbody repair device having a fluid egress path located radially around distal end of the repair device.
Figure 21:
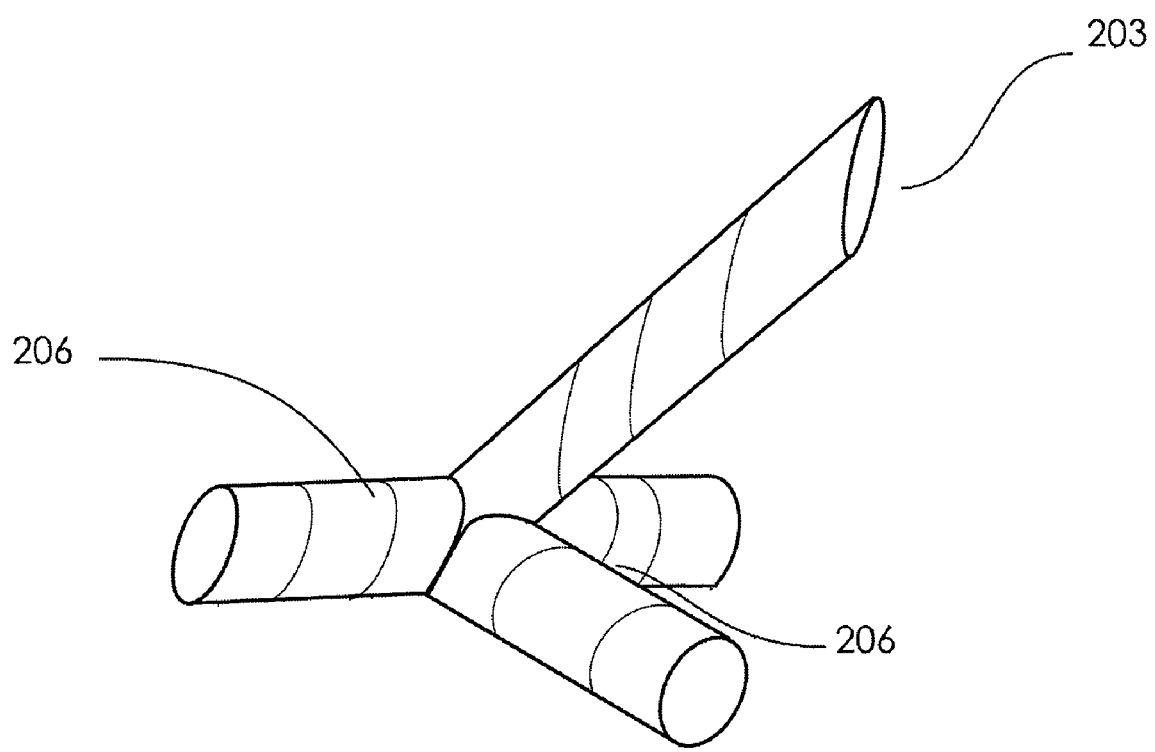
FIG. 21B is a perspective view of the channels within the device shown in FIG. 21A, the channels rendered as pipes.

A cross-sectional view of a bone repair implant 200 embodiment, shown in FIGS. 18 and 19, has a proximal end 201, a distal end 202, and an internal filling channel or lumen 203. The internal filling lumen may have a unidirectional flow control element 204 to allow the passage of the injection device 205 and injected flowable disc-substitute material 108 into a prepared internal disc volume and thereafter restrict the backflow of the material. The back flow control element may be, for example, a plug that is sufficiently compliant that it permits the passage of an injection needle, and is sufficiently resilient that it closes and seals the injection passage after the needle has been withdrawn. FIGS. 20, 21A, and 21B show an alternate embodiment of an implantable bone repair device 200. In this embodiment, the fluid injection does not directly enter the internal disc void, but rather courses through internal access channel or lumen 203 and intersecting one or more diffusion channels 206, distributing around the distal end of the implant device so as to assure a more complete filling of the intra-disc void. FIG. 21B is a perspective view of the lumens within the device shown in FIG. 21A, the lumens rendered as pipes within the solid piece. This embodiment may be particularly suited to use in conjunction with the implantation of a solid intra-disc repair device (FIGS. 16 and 17), where void spaces may remain in the annulus fibrosis of the disc after the disc repair implants are inserted and where supplemental disc substitute material is beneficial to the long term outcome of the procedure.

As described above in general, and in some particularity with regard to the spinal repair device embodiment of FIG. 17, a portion or the substantial entirety of a device may be formed by a porous cage that includes a bone cell preparation. Embodiments such as those depicted in FIGS. 18-27 that include an internal lumen may also be formed from porous cages, or the devices may include forms with portions having walls of mixed composition, some wall portions solid and some wall portions porous. In some embodiments, for example, an internal lumen may be formed from a solid wall, while the external walls are porous.

Figure 22:
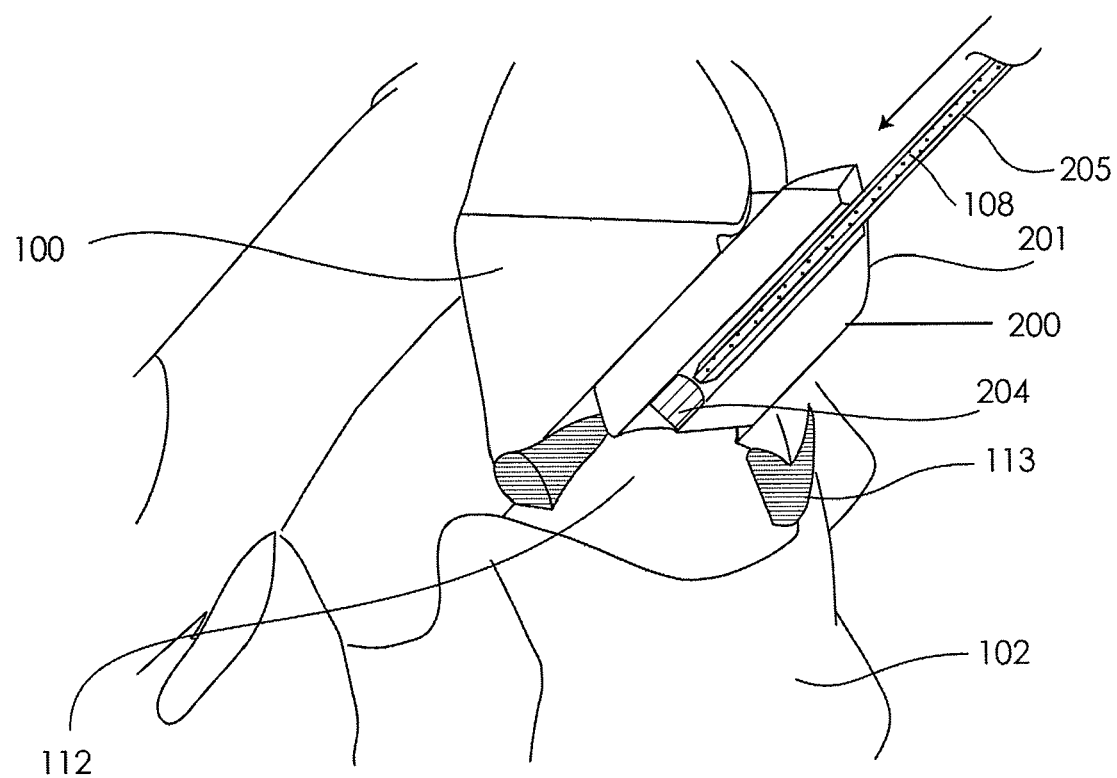
FIG. 22 is a cutaway view through a vertebral body, showing an interbody repair device in situ within the vertebral body and a fluid injection device located entering the central access channel.
Figure 23:
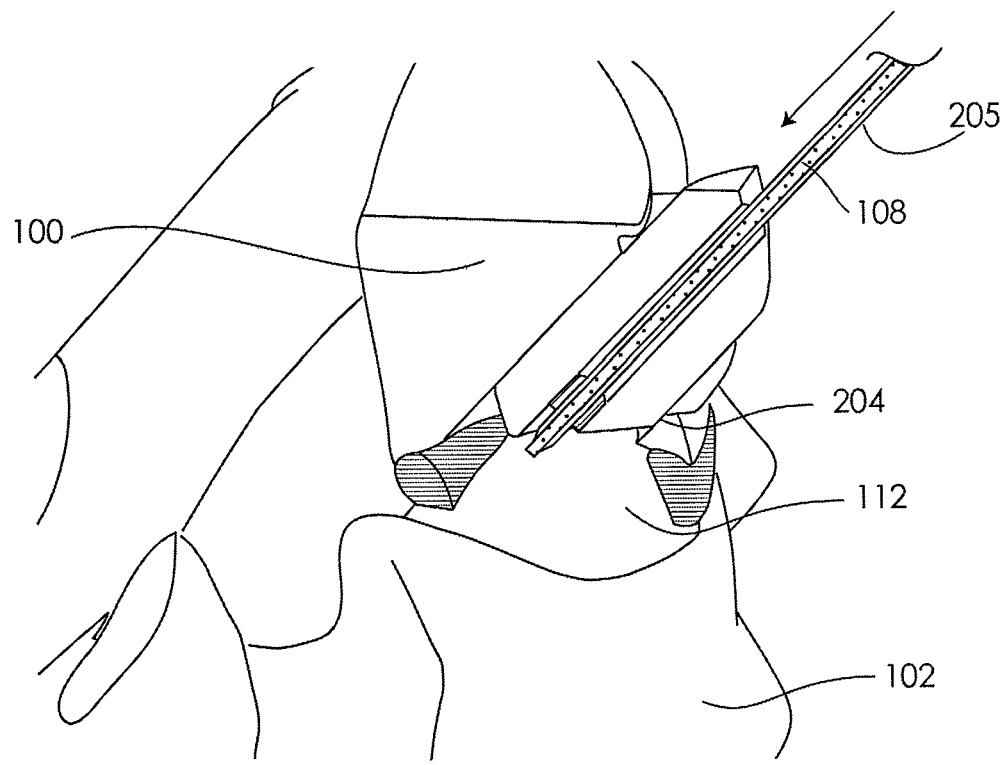
FIG. 23 is a cutaway view through a vertebral body, showing an interbody repair device in situ within the vertebral body and a fluid injection device located within the central access channel, the injection device having penetrated the fluid backflow element and entered the nucleus pulposus volume within the intervertebral disc.

FIG. 22 shows a bone repair implant 200 with an internal fill lumen inserted within the transcorporal access channel within a host vertebral body 100. FIG. 22 further shows an internal disc void 112 contained within the intact annulus fibrosis 113 of the intervertebral disc. Such an internal void is generally the result of a surgical procedure in which the void has been formed by removal of at least a portion of the nucleus pulposis of the disc. The fluid injection device 205 is shown entering the proximal end 201 of implant device 200. FIG. 23 shows the fluid injection device having penetrated the back flow prevention element 204 and entered the intra-disc void 112.

Figure 24:
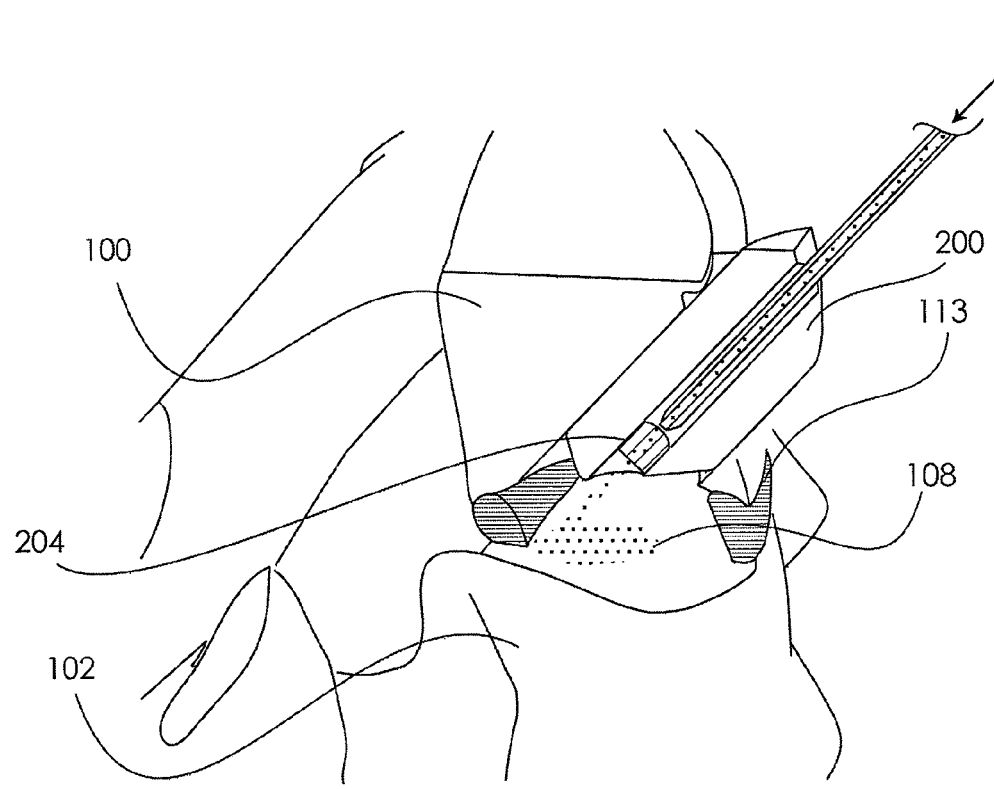
FIGS. 24 and 25 are lateral cutaway views showing disc repair material being injected into the nucleus pulposus volume within the intervertebral disc.
Figure 25:
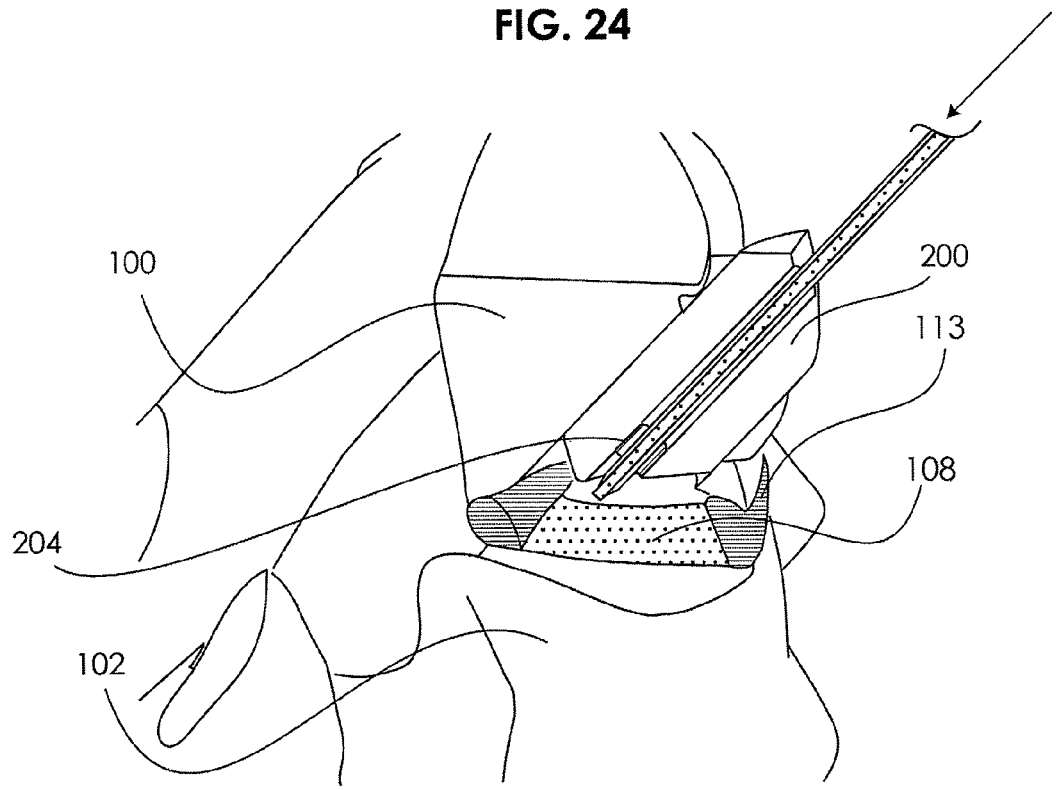
Figure 26:
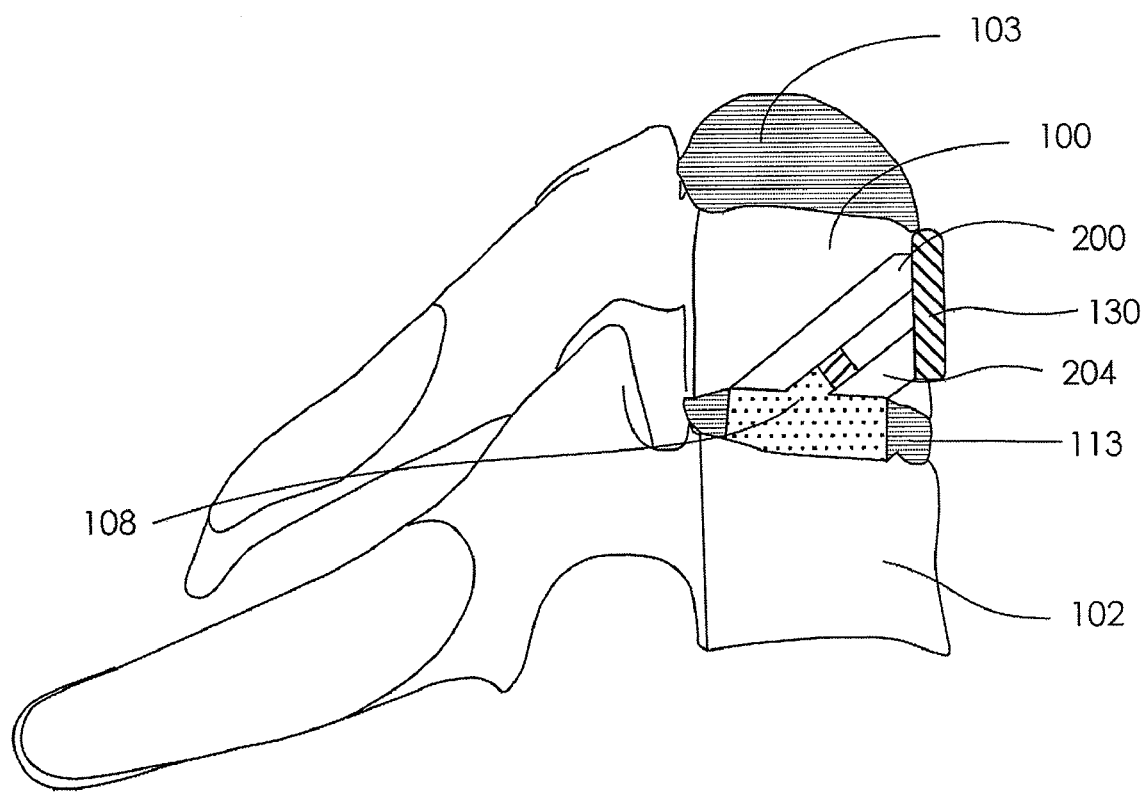
FIG. 26 is a cross section view of the intervertebral disc after it has been filled with a disc repair material and after the injection device has been extracted through the fluid backflow element.

FIGS. 24 and 25 show the progressive injection of a flowable disc substitute material 108 into the internal disc void, the material being constrained by the annulus fibrosis 113 and by the end plate bone tissue of the adjacent vertebral body 102. FIG. 24 shows the injection in an early stage; FIG. 25 shows the injection at stage where the host site is nearly filled with the substitute disc material. The injection process may be regulated by the introduction of a prescribed volume of substitute material, by monitoring back pressure at the injection device, or by other volumetric, pressure or displacement means. FIG. 26 shows the repaired spine section; the fluid injection device has been removed through the backflow prevention element 204, leaving within the annulus fibrosis a restored disc structure, with solidified disc substitute material 108 filling the formerly void space within the disc. In a final step, a bone plate 130 may be fixed to the vertebral body by conventional bone screws so as to resist the expulsion of the bone repair implant 200 and to resist movement so as to promote bone growth of new bone into the device.

In various embodiments of the methods described herein, the vertebral segments may be distracted using currently available methods and tools such as vertebral distractor pins prior to or during the performance of a transcorporal disc repair or replacement procedure.

In various embodiments described herein where a liquid or phase changing material is implanted within the intra-disc volume, it may be advantageous to evacuate gas or fluid from the volume so as to assure optimal filling of the void space with substitute material, and the formation of an appropriate level of substitute material density within the space. The trapping of air within the intervertebral space or within liquid disc substitute material is not a trivial consequence as air is compressible, and for the repaired, restored or substituted disc to function in its normal capacity, the disc volume needs to be resilient, but the total volume is desirably non-compressible. In embodiments of the invention, this gas evacuation may be achieved variously by means of a vent channel integral to the injection device, by means of a vent channel within the bone repair implant device, or by means of a vacuum filling process wherein the gaseous volume is evacuated by a vacuum and a liquid disc material is introduced thereafter into the evacuated volume to relieve the negative pressure within the void, thereby assuring a more complete filling of the complete volume of the void. More generally, the internal cannula or the injector itself may include two channels, one configured for proximal-to-distal flow of liquid disc substitute material, and a second channel configured for distal-to-proximal escape of air that would otherwise remain entrapped. In some embodiments of the method, there may also be egress of liquid disc substitute material through this out-channel as well. This does no particular harm and indeed provides an indication to the operating physician that the intervertebral space (or intradiscal space) is filled. In still other gas-ventable embodiments, the spinal repair device may include longitudinally running folds on the external surface that would allow gas to escape. Some embodiments including these various features may include a cap to be applied to the proximal, external facing surface of the device after injection of the disc substitute material to prevent escape of disc substitute fluid.

Figure 27:
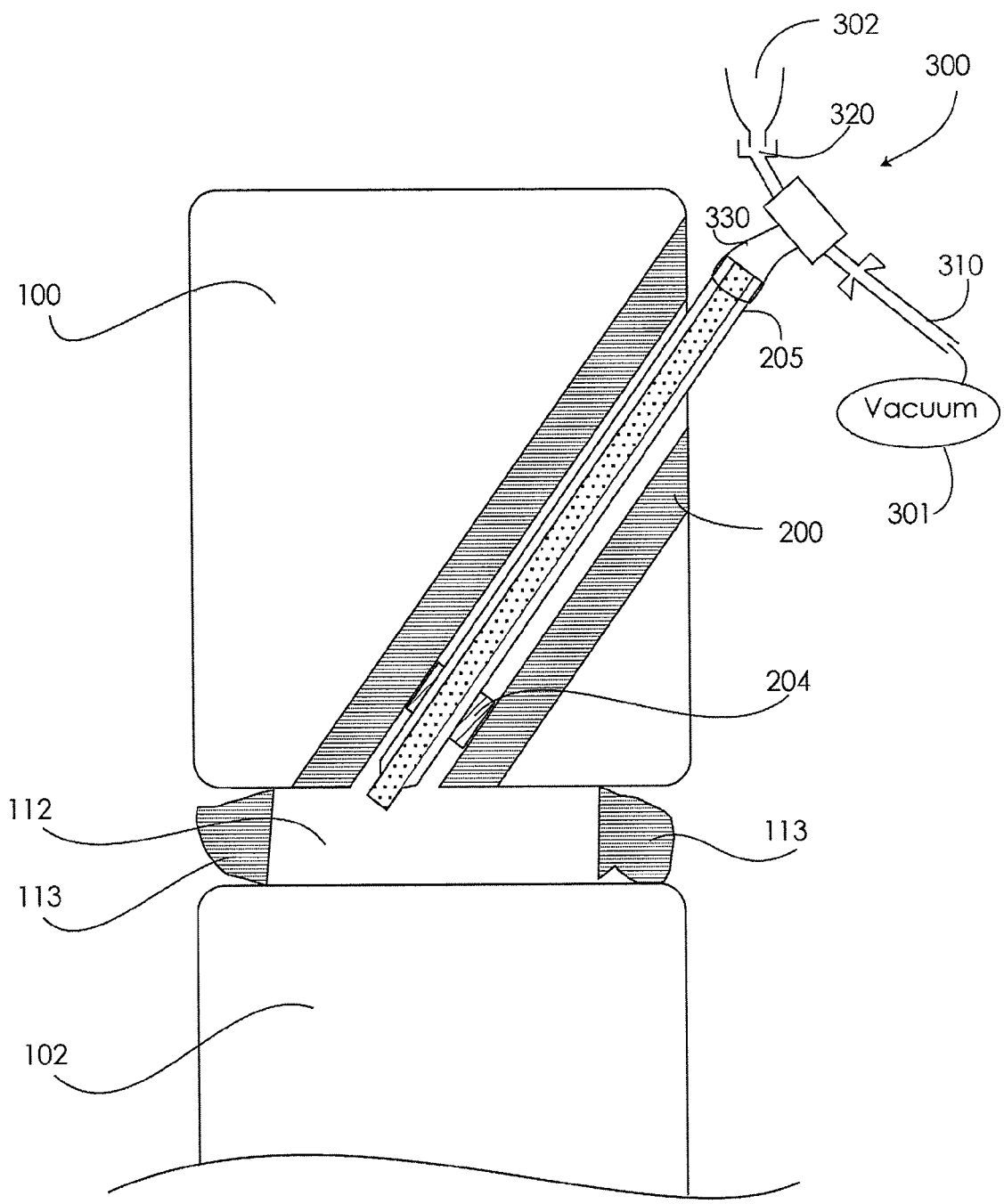
FIG. 27 is a schematic illustration of an embodiment of a vacuum fill system.

FIG. 27 shows a schematic view of an embodiment of a vacuum fill system 300 that may be used in conjunction with a bone repair implant device 200, and as an adjunct to the basic method of using device 200 as described above. In a method making use of the vacuum system 300, a fluid injection device 205 is inserted into the intradiscal void 112. A bi-directional control valve device 301 has two inlet ports 310 and 320 and one outlet port 330, with the outlet port 330 being connected to a fluid injection device 205. A vacuum source 303 is attached to the first inlet port 310 and a fluid reservoir 302 containing the disc repair fluid is attached to the second inlet port 320.

The valve position is set to open an access channel between the vacuum inlet port 310 and the fill device port 330 and a vacuum is created within the intra-disc volume 112. Thereafter the valve device 300 is switched to close the vacuum port 310 and simultaneously open the fluid port 320. The pressure differential between the fluid reservoir 302 and the intra-disc void 113 causes the fluid in the reservoir 302 to flow into the intra-disc void 112, completely filling the internal volume with fluid and avoiding gaseous voids in the disc.

While the exemplary embodiments provided herein all involve an access channel being formed from an anterior surface of the vertebral body towards the nucleus pulposus of the intervertebral disc, such an access channel may alternatively be formed using a lateral or posterior approach. Similarly, while all of the embodiments shown herein involve approaching the nucleus pulposus from a cephalad direction, a caudal approach may be preferable in some instances. Further details of methods and systems for forming a transcorporal access channel into a vertebral body may be found in co-pending U.S. provisional application Ser. No. 60/972,192, filed Sep. 13, 2007, and entitled "Transcorporal spinal decompression and repair system and related method", incorporated herein by reference.

What is claimed is:

1. A method for accessing and repairing an intervertebral disc in the spine comprising:
   engaging a trajectory control apparatus to a non-endplate surface of a vertebral body;
   forming a transcorporal channel in a vertebral body with a trajectory that extends from a non end-plate surface to an end plate where a channel opening communicates into an intervertebral space;
   implanting into the transcorporal channel a spinal repair device sized and configured to occupy at least a portion of the channel, the implanted spinal repair device comprising an internal lumen and a back flow control element located in the lumen;
   evacuating substantially all gas from the intravertebral space; and
   injecting a disc replacement material through the implanted spinal repair device and directly into a void within a space formerly occupied by at least a portion of the intervertebral disc and allowing gas from within the intervertebral space to escape through the spinal repair device during the injecting step, such that the void is substantially entirely filled with disc replacement material.

2. The method of claim 1 wherein forming a transcorporal channel that extends from a non end-plate surface comprises forming the channel from any of an anterior surface, a lateral surface, a posterior aspect of a pedicle, or a posterior, or posterolateral surface.

3. The method of claim 1 wherein the engaging step comprises implanting a bone plate portion of the trajectory control apparatus on the non-endplate surface of the vertebral body and then engaging a bone cutting tool holder portion of the trajectory control apparatus to the bone plate.

4. The method of claim 3 wherein implanting a bone plate on the non-endplate surface of the vertebral body comprises securing it to the surface with one or more fastening elements.

5. The method of claim 3 further comprising removing the bone plate after implanting it.

6. The method of claim 1 further comprising removing at least a portion of the intervertebral disc through the transcorporal channel before injecting the disc replacement material.

7. The method of claim 6 wherein removing at least a portion of the intervertebral disc comprises removing a nucleus pulposis and leaving an annulus fibrosis intact.

8. The method of claim 1 wherein forming the transcorporal channel comprises cutting bone with a bone-cutting tool.

9. The method of claim 1 wherein implanting the spinal repair device comprises compressively engaging an external surface of the spinal repair device with cancellous bone of the host vertebral body.

10. A method for accessing and repairing an intervertebral disc in the spine comprising:
    engaging a trajectory control apparatus to a surface of a host vertebral body;
    forming a transcorporal channel within a host vertebral body, the channel extending from a surface of the host vertebral body on a trajectory toward an intervertebral disc between the host vertebral body and an adjacent vertebral body, and extending at least as far as the end plate of the host vertebral body;
    implanting a spinal repair device configured to fit into the channel and extending into the intervertebral space, the implanted spinal repair device comprising an internal lumen and a back flow control element located in the lumen;
    evacuating substantially all gas from the intravertebral space; and
    injecting a disc replacement material through the implanted spinal repair device and directly into a void within a space formerly occupied by at least a portion of the intervertebral disc and allowing gas from within the intervertebral space to escape through the spinal repair device during the injecting step, such that the void is substantially entirely filled with disc replacement material.

11. The method of claim 10 wherein forming a transcorporal channel that extends from a non end-plate surface comprises forming the channel from any of an anterior surface, a lateral surface, a posterior aspect of a pedicle, or a posterior, or posterolateral surface.

12. The method of claim 10 wherein implanting a spinal repair device comprises placing a distal portion of the device in intimate contact with the end plate tissue of the vertebral body and a proximal portion in intimate contact with cancellous bone tissue within the transcorporal channel.

13. The method of claim 10 wherein the engaging step comprises implanting a bone plate portion of the trajectory control apparatus on the non-endplate surface of the vertebral body and then engaging a bone cutting tool holder portion of the trajectory control apparatus to the bone plate.

14. The method of claim 13 wherein implanting a bone plate on the non-endplate surface of the vertebral body comprises securing it to the surface with one or more fastening elements.

15. The method of claim 13 further comprising removing the bone plate after implanting it.

16. The method of claim 10 further comprising removing at least a portion of the intervertebral disc through the transcorporal channel before implanting the spinal repair device.

17. The method of claim 16 wherein removing at least a portion of the intervertebral disc comprises removing a nucleus pulposis and leaving an annulus fibrosis intact.

18. The method of claim 10 wherein injecting a disc replacement material comprises replacing the portion of the disc with any of a liquid, a liquid that can solidify, a liquid-to-solid phase changing material, a fabric, or a solid, or any combination of these materials.

19. The method of claim 10 wherein forming the transcorporal channel comprises cutting bone with a bone-cutting tool.

20. The method of claim 10 wherein implanting the spinal repair device comprises compressively engaging an external surface of the spinal repair device with an internal surface of the transcorporal channel.

21. The method of claim 10 further comprising injecting a flowable disc material through a lumen in the spinal repair device into the intervertebral space.

* * * * *